United States Patent [19]

Haluska et al.

[11] Patent Number: 4,830,006

[45] Date of Patent: May 16, 1989

[54] IMPLANTABLE CARDIAC STIMULATOR FOR DETECTION AND TREATMENT OF VENTRICULAR ARRHYTHMIAS

[75] Inventors: Edward A. Haluska, Angleton; Stephen J. Whistler, Lake Jackson; Ross G. Baker, Jr.; Richard V. Calfee, both of Houston, all of Tex.

[73] Assignee: Intermedics, Inc., Angleton, Tex.

[21] Appl. No.: 875,218

[22] Filed: Jun. 17, 1986

[51] Int. Cl.⁴ .................. A61N 1/00; H05G 00/00
[52] U.S. Cl. ................................. 128/419 PG
[58] Field of Search ............ 128/419 PG, 419 D, 696, 128/705, 706

[56] References Cited

U.S. PATENT DOCUMENTS

| | | | |
|---|---|---|---|
| 3,693,627 | 9/1972 | Berkovits | 128/419 P |
| 3,698,386 | 10/1972 | Fried | 128/705 |
| 3,698,398 | 10/1972 | Berkovits | 128/419 P |
| 3,832,994 | 9/1974 | Bicher et al. | 128/705 |
| 3,942,534 | 3/1976 | Allen et al. | 128/419 PG |
| 4,280,502 | 7/1981 | Baker, Jr. et al. | 128/419 PG |
| 4,312,356 | 1/1982 | Sowton et al. | 128/419 PG |
| 4,375,817 | 3/1983 | Engle et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,427,011 | 1/1984 | Spurrell et al. | 128/419 PG |
| 4,432,375 | 2/1984 | Angel et al. | 128/706 |
| 4,440,172 | 4/1984 | Langer | 128/419 D |
| 4,473,078 | 9/1984 | Angel | 128/419 D |
| 4,475,551 | 10/1984 | Langer et al. | 128/419 D |
| 4,485,818 | 12/1984 | Leckrone et al. | 128/419 PG |
| 4,523,595 | 1/1985 | Zibell | 128/419 D |
| 4,541,430 | 9/1985 | Elmquist et al. | 128/419 PG |
| 4,552,154 | 11/1985 | Hartlaub | 128/419 PG |
| 4,574,437 | 3/1986 | Segevstad et al. | 128/419 PG |
| 4,577,633 | 3/1986 | Berkovits et al. | 128/419 PG |
| 4,662,377 | 5/1987 | Heilman et al. | 128/419 D |

Primary Examiner—Francis Jaworski
Assistant Examiner—George Manuel
Attorney, Agent, or Firm—Russell J. Egan; Donald R. Greene

[57] ABSTRACT

An implantable cardiac stimulator integrates the functions of bradycardia and anti-tachycardia pacing-type therapies, and cardioversion and defibrillation shock-type therapies. The stimulator is programmable to provide a multiplicity of hierarchical detection algorithms and therapeutic modalities to detect and treat classes of ventricular tachycardia according to position within rate range classes into which the heart rate continuum is partitioned, and thus according to hemodynamic tolerance, with backup capabilities of defibrillation and bradycardia pacing at the higher and lower regions of the rate continuum outside the range of the ventricular tachycardia classes. Aggressiveness of the therapy is increased with elapsed time and increasing heart rate, and detection criteria are relaxed with increasing heart rate and thus with increasing hemodynamic intolerance of the tachycardia.

65 Claims, 14 Drawing Sheets

AGC
AMPLIFIER
SECTION

BANDPASS AMPLIFIER SECTION

QUAD COMPARATOR SECTION

OUTPUT SHORT CIRCUIT PROTECTION

EXAMPLE: COMPARATOR INPUT SIGNAL
WITH LOGIC OUTPUTS

HIGH VOLTAGE GENERATION & OUTPUT SECTION (& DEVICE OUTPUT TERMINALS)

FIG.13 TRANSFORMER ISOLATED SWITCH DRIVER CIRCUIT

ISOLATED HIGH VOLTAGE
GENERATION CIRCUIT

HIGH VOLTAGE OSCILLATOR

HIGH VOLTAGE REGULATOR / PRIORITY POWER SEQUENCER

IMPLANTABLE CARDIAC STIMULATOR FOR DETECTION AND TREATMENT OF VENTRICULAR ARRHYTHMIAS

BACKGROUND OF THE INVENTION

1. Field of the Invention

The present invention relates generally to medical devices; and more particularly to an implantable cardiac stimulator that provides a hierarchical approach to the treatment of ventricular arrhythmias, utilizing combinations of pacing, cardioverting, and defibrillating therapies.

2. Relevant Background

In the normal human heart, the sinus node generally located near the junction of the superior vena cava and the right atrium constitutes the primary natural pacemaker by which rhythmic electrical excitation is developed. The cardiac impulse arising from the sinus node is transmitted to the two atrial chambers, or atria, at the right and left sides of the heart. In response to this excitation, the atria contract, pumping blood from those chambers into the respective ventricular chambers, or ventricles. The impulse is transmitted to the ventricles through the atrioventricular (A-V) node, or junction, and via a conduction system comprising the bundle of His, or common bundle, the right and left bundle branches, and the Purkinje fibers. In response, the ventricles contract, the right ventricle pumping unoxygenated blood through the pulmonary artery to the lungs and the left ventricle pumping oxygenated (arterial) blood through the aorta and the lesser arteries to the body. The right atrium receives the venous (unoxygenated) blood from the upper part of the body (head, neck and chest) via the superior vena cava, or upper great vein, and from the lower part of the body (abdomen and legs) via the inferior vena cava, or lower great vein. The blood oxygenated by the lungs is carried via the pulmonary veins to the left atrium.

This action is repeated in a rhythmic cardiac cycle in which the atrial and ventricular chambers alternately contract and pump, then relax and fill. One-way valves along the veins, between the atrial and ventricular chambers in the right and left sides of the heart (the tricuspid valve and the mitral valve, respectively), and at the exits of the right and left ventricles (the pulmonary and aortic valves, respectively) prevent backflow of the blood as it moves through the heart and the circulatory system.

The sinus node is spontaneously rhythmic, and the cardiac rhythm originating from that primary natural pacemaker is termed sinus rhythm. This capacity to produce spontaneous cardiac impulses is called rhythmicity, or automaticity. Some other cardiac tissues possess this electrophysiologic property and hence constitute secondary natural pacemakers, but the sinus node is the primary pacemaker because it has the fastest spontaneous rate. The secondary pacemakers tend to be inhibited by the more rapid rate at which impulses are generated by the sinus node.

The resting rates at which sinus rhythm occurs in normal persons differ from age group to age group, generally ranging between 110 and 150 beats per minute ("bpm") at birth, and gradually slowing in childhood to the range between 65 and 85 bpm usually found in adults. The resting sinus rate (hereinafter termed simply the "sinus rate") varies from one person to another, and despite the aforementioned usual adult range, is generally considered to lie anywhere between 60 and 100 bpm (the "sinus rate range") for the adult population.

A number of factors may affect the rate of sinus rhythm within the sinus rate range, and some of those factors may slow or accelerate the rate sufficiently to take it outside the sinus rate range. The slower rates (below 60 bpm) are called sinus bradycardia, and the higher rates are termed sinus tachycardia. In particular, sinus tachycardia observed in healthy persons arises from various factors which may include physical or emotional stress (exercise or excitement), consumption of beverages containing alcohol or caffeine, cigarette smoking, and ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from normal sinus rate range. Arrhythmia rates which exceed the upper end of the sinus rate range are termed tachyarrhythmias. Healthy persons usually experience a gradual return to the sinus rate after removal of the factor(s) giving rise to sinus tachycardia, and hence, treatment of the arrhythmia is not necessary unless it is found to be attributable to disease. Abnormal arrhythmias (which are hereinafter simply termed "arrhythmias", and in the case of abnormal tachyarrhythmias, simply termed "tachyarrhythmias", to mean arrhythmias associated with cardiac or other disease, and which are to be contrasted with arrhythmias not associated with disease and for which the modifier "normal" will hereinafter sometimes be used), however, may require special treatment, and in some instances require immediate emergency treatment toward preventing sudden death of the afflicted individual.

It is a principal object of the present invention to provide an improved medical device for treating arrhythmias, which employs a hierarchical approach to such treatment.

The electrophysiologic properties of the heart include excitability and conductivity, as well as the aforementioned automaticity (rhythmicity). It has been observed that alteration or impairment of any of these interrelated properties may result in cardiac arrhythmias. For example, A-V junctional tachycardia is an acceleration of the ectopic automaticity that may occur despite the generation of cardiac impulses at the sinus rate by the sinus node.

Excitability, which is the property of cardiac tissue to respond to a stimulus, varies with the different periods of the cardiac cycle. There is an inability of the cardiac tissue to respond to a stimulus during the portion of the refractory period termed the absolute refractory phase (approximating the interval of contraction, from the start of the QRS complex to the commencement of the T wave of the electrocardiogram), and a lower than usual response during another portion of the refractory period constituting the initial part of the relative refractory phase (coincident with the T wave). In the mid-portion of the relative refractory phase corresponding to the top of the T wave, referred to as the vulnerable period, the heart is prone to develop fibrillation in response to even a low intensity stimulus. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

Excitability of the various portions of the cardiac tissue differs according to their degree of refractoriness, with ventricular tissue being more refractory than atrial tissue and less refractory than A-V junctional tissue, for example. Similarly, the different portions of the heart vary significantly in conductivity, a related electrophysiologic property of cardiac tissue that determines the speed with which cardiac impulses are transmitted. For example, ventricular tissue is less conductive than atrial tissue and more conductive than A-V junction tissue. The longer refractory phase and slower conductivity of the A-V junctional tissue give it a significant natural protective function, which will be described presently.

Disruption of the natural pacemaking and propagation system as a result of aging or disease is commonly treated by artificial cardiac pacing, by which rhythmic electrical discharges are applied to the heart at a desired rate from the implanted artificial pacemaker (referred to throughout the remainder of this document simply as a "pacemaker"). In its simplest form, the pacemaker consists of a pulse generator powered by a self-contained battery pack, and a lead including at least one stimulating electrode electrically connected to the pulse generator. The lead is typically of the catheter type for intravenous insertion to position the stimulating electrode(s) for delivery of electrical impulses to excitable myocardial tissue in the appropriate chamber(s) in the right side of the patient's heart. However, in some instances epicardial electrodes are implanted by surgically splitting the patient's chest or other well known techniques, and suturing or screwing them in to the epicardium. Typically, the pulse generator is surgically implanted in a subcutaneous pouch in the patient's chest. In operation, the electrical stimuli are delivered to the excitable cardiac tissue via an electrical circuit that includes the stimulating and reference electrodes, and the body tissue and fluids.

A pacemaker operates in one of three different response modes, namely, asynchronous (fixed rate), inhibited (stimulus generated in absence of specified cardiac activity), or triggered (stimulus delivered in response to specified cardiac activity). The demand ventricular pacemaker, so termed because it operates only on demand, has been the most widely used type. It senses the patient's natural heart rate and applies stimuli only during periods when that rate falls below the preset pacing rate.

Pacemakers range from the simple fixed rate device that provides pacing with no sensing function, to the highly complex model implemented to provide fully automatic dual chamber pacing and sensing functions. The latter type of pacemaker is the latest in a progression toward physiologic pacing, that is, the mode of artificial pacing that restores cardiac function as much as possible toward natural pacing.

Historically, pacemakers have been employed primarily for the treatment of bradyarrhythmias, but over the past several years cardiac pacing has found significantly increasing usage in the management of tachyarrhythmias. Anti-tachyarrhythmia pacemakers take advantage of the aforementioned inhibitory mechanism that acts on the secondary natural pacemakers to prevent their spontaneous automaticity, sometimes termed "postdrive inhibition" or "overdrive inhibition". In essence, the heart may be driven (stimulated) with a faster than normal pacing rate to suppress ectopic activity in the form of premature atrial or ventricular contractions (extrasystoles) that might otherwise initiate supraventricular or ventricular tachycardia, flutter (typically, a tachyarrhythmia exceeding 200 bpm), or fibrillation; or to terminate an existing tachyarrhythmia. It should be noted that premature ventricular contractions (PVCs) may be observed in persons without evidence of heart disease.

The pulses delivered to the heart for pacing therapy need only be of sufficient magnitude to stimulate the excitable myocardial tissue in the immediate vicinity of the pacing electrode. In contrast, another technique for terminating tachycardias, termed cardioversion, utilizes apparatus to shock the heart with one or more current or voltage pulses of generally considerably higher energy content than is delivered in pacing pulses. Whether pacing or cardioverting therapy is employed in an effort to terminate a tachycardia, a considerable risk is present that the treatment itself may precipitate fibrillation.

Defibrillation ("DF"), the method employed to terminate fibrillation, involves applying one or more high energy "countershocks" to the heart in an effort to overwhelm the chaotic contractions of individual tissue sections, allow reestablishment of an organized spreading of action potential from cell to cell of the myocardium, and thus restore the synchronized contraction of the mass of tissue. The term "cardioversion" is sometimes used broadly to include DF, but in the present document, a distinction is maintained between the two terms and the techniques designated by them. In the great majority of cases, atrial fibrillation ("AF") is hemodynamically tolerated and not life-threatening because the atria provide only a relatively small portion (typically on the order of 15 to 20 percent) of the total cardiac output, i.e., the volume of blood pumped by the heart per unit time. Indeed, a technique frequently used in the past for terminating atrial flutter involves stimulating the atrium with artificial pacing pulses delivered at a rate higher than the flutter rate to convert the flutter to fibrillation. Within a relatively brief interval following cessation of the pacing, the heart usually reverts to normal sinus rhythm on its own. During this time, the tissue remains healthy because it is continuing to receive a fresh supply of oxygenated blood as a result of the continued pumping action of the ventricles.

Atrial tachycardia ("AT") may also be hemodynamically tolerated because of the aforementioned natural protective property of the A-V junctional tissue (sometimes referred to as "functional A-V block") attributable to its longer refractory period and slower conductivity than atrial tissue. This property renders the A-V junctional tissue tissue unable to fully respond to the more rapid atrial contractions. As a result, the ventricle may miss every other or perhaps two of every three contractions in the high rate atrial sequence, resulting in 2:1 or 3:1 A-V conduction, and thus maintain relatively strong cardiac output and near-normal rhythm.

Nevertheless, in cases where the patient is symptomatic or at high risk in events of AT or AF—for example, instances where the patient suffers from ventricular heart disease and consequent reduction of ventricular pumping capability, with a correspondingly greater contribution by the atria to cardiac output—special treatment of these atrial disorders is necessitated. The methods of treatment commonly prescribed by the physician include medication, drugs, pacing therapy, cardiac shock therapy, and in some cases, surgically creating an A-V block and implanting a ventricular pacemaker.

In contrast to AT, cardiac output is considerably diminished during an episode of ventricular tachycardia ("VT") because the main pumping chambers of the heart, the ventricles, are only partially filled between the rapid contractions of those chambers. Moreover, VT presents a significant risk of acceleration of the arrhythmia into ventricular fibrillation ("VF"), either spontaneously or in response to treatment of the VT. As in the case AF, ventricular fibrillation ("VF") is characterized by rapid, chaotic electrical and mechanical activity of the excitable myocardial tissue, but in contrast to AF, VF manifests an instantaneous cessation of cardiac output as the result of the ineffectual quivering of the ventricles. Unless cardiac output is restored almost immediately after the onset of VF, tissue begins to die for lack of oxygenated blood, and death will occur within minutes.

Accordingly, it is a further object of the present invention to provide an improved medical device for treating ventricular tachyarrhythmias, including ventricular tachycardia, flutter, and fibrillation, with improved techniques for detecting the arrhythmia and for distinguishing it from normal high rates, and using a hierarchical approach to the aggressiveness and delivery of therapies.

The pulse energy requirements for cardioversion and defibrillation overlap to an extent, ranging from as low as about 0.05 joule to approximately 10 joules for cardioversion and from about 5 joules to approximately 40 joules for DF. The energy level required differs from patient to patient, and depends on type of pulse waveform and electrode configuration used, as well as various other known factors.

Traditionally, practical defibrillators have been characterized by rather bulky electrical apparatus for applying a high-energy pulse through the heart via paddles placed at predetermined locations on the patient's thorax. Over the past several years, however, implantable cardioverters and defibrillators have been proposed for use in detecting and treating VT and/or VF. In 1970, M. Mirowski et al. and J. C. Schuder et al. separately reported in the scientific literature their independent proposals of a "standby automatic defibrillator" and a "completely implanted defibrillator", respectively, and experimental results in dog tests. Since that time, a vast number of improvements in implantable cardioverters and defibrillators, including electrode placement using extrapericardial patches or transvenous catheters, has been reported in the scientific literature and patent publications. A fairly representative sampling is as follows:

U.S. Pat. No. 3,805,795 issued Apr. 23, 1974 to Deniston et al. describes a defibrillator circuit with implanted electrodes for delivering defibrillating pulses to the heart only if separate signals respectively indicative of electrical and mechanical activity are both absent for a predetermined period of time, and in which the first pulse delivered is of lower energy content than succeeding pulses.

U.S. Pat. No. 4,114,628 issued Sept. 19, 1978 to Rizk describes a demand pacemaker with an automatically adjusted threshold, and having an operating mode in which a difibrillating pulse is automatically applied to the patient's heart in the absence of cardiac activity for a predetermined period of time.

U.S. Pat. No. Re. 27,652 to Mirowski et al. describes an automatic implantable defibrillator in which a preset delay is imposed between successive shocks, and in which further shocks are inhibited following successful defibrillation.

U.S. Pat. No. 4,181,133 issued Jan. 1, 1980 to Kolenik et al. describes a programmable implantable pacemaker which provides the dual functions of demand pacing and standby cardioversion of tachycardias. U.S. Pat. No. 4,300,567 issued Nov. 17, 1981 to Kolenik et al. describes an implantable automatic defibrillator adapted to deliver a high energy defibrillating pulse in one mode and lower energy cardioverting pulses in another mode.

Generally speaking, the implantable defibrillators of the prior art detect ECG changes and/or absence of a "mechanical" function such as rhythmic contractions, pulsatile arterial pressure, or respiration, and in response deliver a fixed therapy typically consisting of one or more shocking pulses of preset waveform and energy content. If any other cardiac therapy is available from the device, such as cardioversion for treatment of tachycardia, it too is delivered according to a fixed plan in response to conventional detection of the specific arrhythmia. While many of these proposed devices appear to be capable of functioning as they are described in the literature, and may become widely available in the future, they offer little or no flexibility of therapy regimen or capability to detect subtle changes in the arrhythmia to be treated and to respond with appropriate therapy.

Accordingly, it is another general object of the present invention to provide an implantable cardiac stimulator adapted to arrest a detected arrhythmia by selectively delivering any of a plurality of sequences of dissimilar therapies depending on the degree of hemodynamic tolerance (or intolerance) of the patient to the detected arrhythmia.

A related object of the invention is to provide such an implantable cardiac stimulator further adapted to detect a change in the arrhythmia and to respond thereto by selective delivery of a therapy sequence which may be more or less aggressive (in terms of likelihood of arresting the arrhythmia) than the immediately preceding therapy sequence, depending on direction and extent of the arrhythmia change.

In copending U.S. patent application Ser. No. 765,047, filed Aug. 12, 1985 (hereinafter referred to as "the 765,047 application"), assigned to the same assignee as is the present invention, an antitachycardia pacemaker is disclosed in which a microprocessor is programmed to detect pace-terminable tachycardias, such as reentrant tachycardias (i.e., tachycardias characterized by a premature beat and constant coupling interval because of localized refractoriness), using a detection algorithm which selectively includes high rate, rate stability, sudden onset and sustained high rate tests. When a tachycardia is detected, the pacemaker responds in a programmed fashion toward terminating the tachycardia by applying programmed bursts of stimulating pulses to the heart in accordance with selected treatment modalities. If a detected tachycardia is similar to a previous successfully terminated tachycardia, the pacemaker programming will re-apply the previous successful treatment modality in an initial attempt to terminate the new tachycardia. The start delay and pulse-to-pulse interval may be defined as fixed program values, or as adaptive values derived as a percentage of the detected high rate interval. If a burst is generated, the start delay of the burst or the pulse-to-pulse interval of the burst may be scanned by incrementing or decrementing the values of these parameters a preseleceted number of steps or by incrementing and decrementing the parameters in a predefined search pattern. Alternatively, the intervals of the pulses within a burst are automatically decremented in the autodecremental mode.

The antitachycardia pacemaker of the 765,047 application represents a distinct and significant improvement over previous devices of that general type, in such aspects as the nature of the detection system, techniques for distinguishing pace-terminable tachycardias from other tachycardias, and application of pacing therapies toward extinguishing such detected pace-terminable tachycardias. However, that device is somewhat one-dimensional in its detection and treatment capabilities, to a great extent being restricted to pace-terminable atrial tachycardias and pacing therapies, although it serves that medical application quite well.

Therefore, a more specific object of the present invention is to provide an improved implantable medical device adapted to detect ventricular tachycardias and other arrhythmias throughout the heart rate continuum, and automatically responsive to such detection to selectively deliver one or more of a plurality of predetermined therapies, including bradycardia and antitachycardia pacing-type therapies and cardioverting and DF shock-type therapies, in different regimens of dissimilar aggressiveness of treatment according to the degree of hemodynamic tolerance or intolerance of the detected arrhythmia.

Antitachycardia pacemakers are typically utilized against atrial tachycardia, and are generally unsuitable for treating VT because of the risk of accelerating the latter to VF and the inability of such devices to respond effectively to the acceleration.

Accordingly, another object of the invention is to provide a medical device suitable for delivering antitachycardia pacing therapy for managing ventricular tachycardias, and having additional or backup capabilities for terminating VF in the event of acceleration, and thereby to lessen the risk associated with using pacing therapies to treat VT.

SUMMARY OF THE INVENTION

The present invention integrates the functions of bradycardia and anti-tachycardia pacing-type therapies, and cardioversion and defibrillation shock-type therapies, to provide a coordinated approach to the management and treatment of ventricular arrhythmias, including VT and VF. A very significant aspect of this coordinated approach is that it provides flexible sequencing among the therapies, with appropriate regard to hemodynamic tolerance (or intolerance) of the patient to the detected arrhythmia, and sophisticated detection of arrhythmias together with means for distinguishing those episodes for which treatment is required (such as reentrant tachycardias) from those which are not associated with cardiac or other disease (such as exercise-generated sinus tachycardias). The coordinated approach of the invention further takes into account and deals effectively with the risk of acceleration of a tachycardia, as well as with considerations of longevity of the power source for an implantable device, and of patient acceptance of the device.

According to the invention, a multiplicity of hierarchical detection algorithms and hierarchical therapeutic modalities are selectively available to the physician and applicable to detect and treat classes of ventricular tachycardia according to their respective positions in the heart rate continuum, and thus according to hemodynamic tolerance or intolerance of the patient to the tachycardia, with backup capabilities of defibrillation and bradycardia pacing for cardiac arrhythmias at the respective higher and lower regions of the rate continuum, outside the overall VT range.

A feature of the invention is the application of the principle that aggressiveness of the therapy should be increased with elapsed time and with increasing abnormal heart rate. Further, in one of its aspects, the invention provides the physician with complete control over the aggressiveness of the therapy for any particular patient and tachyarrhythmia, utilizing a hierarchical approach to treatment by the implantable medical device. Moreover, the methodology employed in developing the hierarchy is such that physician control is imparted over a wide variety of possible therapy regimens ranging from the basic to the highly complex, with relatively simple programming of the device.

In one embodiment, a cardiac stimulator for detecting and treating ventricular arrhythmias permits selective partitioning of the heart rate continuum into a plurality of contiguous tachycardia classes of progressively higher rate ranges, the lowest and highest of these classes being bounded respectively by regions of the continuum denoting sinus rate and fibrillation. Each of the rate ranges and the latter regions may be arbitrarily designated by the physician, as may be necessary to meet the particular needs of the patient's condition or disorder and the flexibility of the therapy regimens to be prescribed by the physician. The stimulator includes a hierarchical detection system for detecting cardiac episodes indicative of arrhythmia and for distinguishing between normal and abnormal tachycardias among the detected episodes, using criteria of greater or lesser stringency depending on the location of the episode in the rate continuum. In response to detection of an arrhythmia within or outside any of the designated tachycardia classes, the stimulator will automatically deliver one or more therapies according to the physician's exact prescription (based on various factors including, for example, specific patient data, arrhythmia rate, episode longevity and acceleration or deceleration). In this particular embodiment, the available therapies include bradycardia pacing, anti-tachycardia pacing, cardioverting shocks, and DF shocks, which may be delivered separately or in any combination (according to the physician's prescription) to treat the detected arrhythmia, and more particularly, with an ascending order of aggressiveness of the therapy according to the degree of hemodynamic intolerance of the arrhythmia.

Therefore, it is another specific object of the present invention to provide a ventricular arrhythmia detection and treatment device, preferably for implantation in the patient, in which the heart rate spectrum may be selectively divided into contiguous, successive regions of progressively higher rate ranges representative of different tachycardia classes between the sinus region and the fibrillation region, for automatically delivering preselected therapy regimens of different degrees of aggressiveness of treatment in response to detection of an arrhythmia in any region above or below the sinus region, according to the specific region in which the arrhythmia is detected.

Another feature of the invention is that the hierarchy of detection criteria algorithms developed for detecting arrhythmias in the various rate ranges designated by the physician, may be assigned to the respective rate ranges such that the criteria are progressively less stringent for detecting episodes in progressively higher rate ranges (and thus detection criteria are relaxed with increasing hemodynamic intolerance of the arrhythmia).

A further specific object of the invention is to provide such an arrhythmia detection and treatment device in which redetection to determine the presence or absence of the arrhythmia (including any acceleration or deceleration thereof) upon delivery of the prescribed therapy regimen in response to the earlier detection, may employ fewer than the tests used for the original detection.

Still another object of the present invention is to provide such an arrhythmia detection and treatment device in which the delivery of the therapy sequences for treatment of the arrhythmia may be altered while the episode is in progress, according to a preselected control option.

BRIEF DESCRIPTION OF THE DRAWINGS

The above and still further objects, features and advantages of the present invention will become apparent from the following detailed description of a presently preferred embodiment, taken in conjunction with the accompanying drawings, in which.

DETAILED DESCRIPTION OF A PREFERRED EMBODIMENT

Figure 1A:
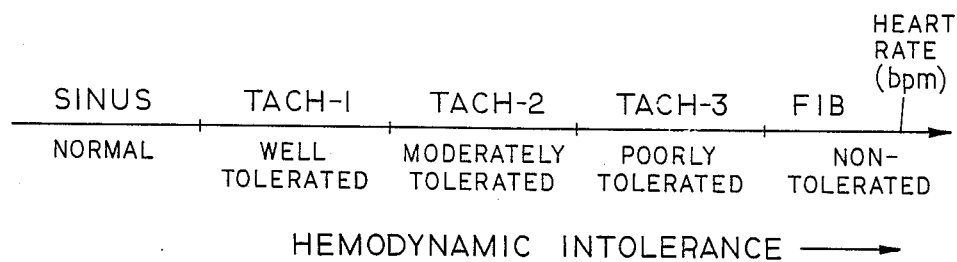
FIGS. 1a and 1b are diagrams illustrating the manner in which the heart rate continuum is divided (partitioned) into arrhythmia classes according to the invention.

For the sake of clarity, the invention will be described initially in the context of operation of a presently preferred embodiment comprising a cardiac stimulator (sometimes referred to herein as the "stimulator", "medical device", or "device") having combined pacemaker, cardioverter and defibrillator functions, and which, if desired, is implantable in the abdomen of the cardiac patient. Description of the significant structural details of the stimulator will be deferred to a subsequent portion of this specification.

In describing the operation of the presently preferred embodiment, it will become apparent to the reader that the principal function of this embodiment is to manage and treat tachycardia, and more specifically, VT, using therapies involving pacing stimulation pulses or cardioverting shocks, or various combinations of those therapies, with the backup or standby functions of DF and bradycardia pacing. However, it will also be recognized that the principles of the invention are applicable to various other practical implementations.

It was noted in the background section, above, that treatment of VT with pacing or cardioverting therapy carries a significant risk of acceleration to VF and with it, imminent death of the patient. The nature of the risk is such that in some instances it has tended to limit aggressive treatment of VT, notwithstanding the undesirable physiological symptoms (such as syncope, lightheadedness, and the like) associated with that cardiac episode or event. Difficult issues have arisen with respect to the proper management of therapies, and as to whether and how the aggressiveness of the therapy may be increased with increasing hemodynamic intolerance of the patient to VT, and/or with the passage of time.

The availability of the DF capability of the cardiac stimulator provides the physician with the luxury of prescribing in appropriate cases an increasingly aggressive regimen, according to the hierarchical approach and to other features of the invention as will be appreciated from the ensuing description, with the attendant ability to quickly detect and treat VF in the event of acceleration of the VT. As a result, the risk of a fatal cardiac event is substantially reduced.

On the other hand, as a result of alterations of tissue excitability or conductivity during or immediately after treatment of VT, or the application of ventricular DF, or dysfunction, the patient's heart may become asystolic (that is, cease spontaneous electrical activity and contraction of the chambers). The period of time of such an occurrence may be brief, but during that period the heart's pumping action ceases and it is essential that immediate circulatory support be provided. To that end, the bradycardia pacing capability of the stimulator provides a standby function to deliver the necessary stimuli to pace the heart during any such period, until normal heart activity is detected.

Further, the standby pacing function is triggered into operation by logic circuitry in the event of a failure of the timing and therapy control functions of the cardiac stimulator, as a fail-safe feature for pacemaker dependent patients. An additional feature is that the pacemaker function provides non-competitive pacing (that is, paces only when not in competition with the patient's normal heart action) to avoid precipitating VT or VF, as neither of them would be treatable by the cardiac stimulator in circumstances where the bradycardia pacing has been initiated in response to the loss of the stimulator's timing and control functions.

With reference now to FIG. 1a, according to one significant aspect of the invention, the heart rate continuum or spectrum is divided, or partitioned, into a multiplicity of regions defining contiguous, successive heart rate ranges consistent respectively with sinus rhythm, designated SINUS at the lower end of the continuum of interest, progressively higher rate ranges associated with VT, respectively labeled TACH-1, TACH-2, and TACH-3, and into and beyond the commencement of rates associated with VF, designated FIB at the upper end of the continuum of interest.

It will be observed from FIG. 1a that the spectrum is preferably partitioned such that the rate ranges (regions) so defined are representative of respective degrees of hemodynamic tolerance of the patient to cardiac rates in those regions. Thus, in the illustrative example of FIG. 1a, the ascending order of the three VT regions depicts well tolerated, moderately tolerated, and poorly tolerated classes of tachycardia, respectively. Although three tachycardia classes are utilized in the presently preferred embodiment, the actual number of such classes may be greater or fewer than three depending on the judgment of the physician regarding the management of arrhythmias and the prescription of therapy regimens for a particular patient, as will become clear from the discussion of therapy considerations below. As indicated in FIG. 1a, and to be expected, heart rates in the SINUS region are normal (at least that portion of the region considered to be in the normal resting sinus rate range, discussed above), whereas rates in the FIB region are not tolerated at all.

Figure 1B:
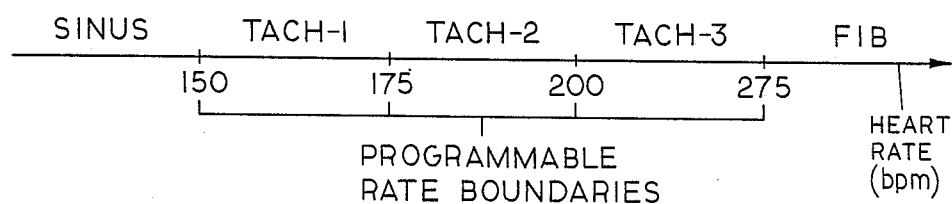

The overall continuum of interest may be left unbounded and the rate ranges of the tachycardia classes selectively designated by assigning specific rate numbers to the boundaries of those regions with each other and with the SINUS and FIB regions. By way of example and not of limitation, the lower and upper boundaries of the TACH-1 region may be set at 150 and 175 bpm, and of the TACH-3 region at 200 and 275 bpm, respectively, coincidentally defining the rate range of the TACH-2 region as well as the upper boundary of the SINUS region and the lower boundary of the FIB region, as illustrated in FIG. 1b.

Each boundary rate separating adjacent regions is selectively adjustable by the physician during the programming or reprogramming of the cardiac stimulator (using a programmer unit external to the stimulator), based on the particular patient data, including age, nature of the disorder, and any other factors the physician may deem pertinent to the establishment of the specific rate ranges occupied by the regions. These programmed boundary rates are stored in a computer memory associated with a central microprocessor within the cardiac stimulator, via an implanted antenna and data transmission network of the stimulator, as will be described presently. It is worthy of emphasis that this flexibility of designating the overall rate continuum of interest, and of designating the boundaries of the individual tachycardia classes, is a significant feature of the invention.

In addition to allowing the physician to designate the arrhythmia classes to be utilized by the device, the present invention gives the physician the capability to prescribe any of a plurality of basic therapies for treatment of the arrhythmias, to specify the detailed nature (i.e., the fine structure) of each of those therapies, to designate the sequence in which the therapies are to be delivered in response to a detected arrhythmia in any of the designated arrhythmia regions, and to select the algorithms for detecting arrhythmias in each region.

For example, in the presently preferred embodiment of the stimulator any of four basic therapies may be selectively designated to treat respective detected events in each of the four arrhythmia classes TACH-1, TACH-2, TACH-3, and FIB. It should be emphasized that the number of basic therapies may be greater or fewer than the number of arrhythmia classes, and that there is no particular significance to the common number of them in this embodiment. It is also important to note that the number and complexity of the basic therapies, and of other stored and/or programmable data functions described herein, are limited from a practical standpoint only (not conceptually) by memory type and capacity in the cardiac stimulator and associated programming unit.

In essence, the basic therapies may be defined in any desired manner from the group consisting of all of the potential therapies which may be delivered by the device, each of the deliverable therapies being alterable (again, within the practical limitations of the device) in terms of its fine structure. Thus, the device gives the physician the capability to alter the fine structures of the deliverable therapies, and to define them, as he or she chooses, as the basic therapies. The latter may then be assigned separately or in any combination as a plurality of regimens or sequences appropriate for treatment of arrhythmias in the respective designated rate ranges, tailored to the particular patient.

For example, one definition of the four basic therapies of the present embodiment could be as follows:
THERAPY-A: non-aggressive pacing bursts;
THERAPY-B: aggressive pacing bursts;
THERAPY-C: cardioverting shocks; and
THERAPY-D: defibrillating shocks.
However, THERAPIES A and B could equally well both be defined as aggressive pacing bursts, differing in fine structure only, or THERAPIES A, B and C could equally well be defined as cardioverting shocks, again differing only in fine structure, or each of the therapies could be defined in any other manner desired by the physician, limited only by the range of therapies deliverable by the stimulator.

It will be observed that the alphabetical order of the basic therapies corresponds to their relative aggressiveness in treating arrhythmias, but there is no other intended relationship between the alphabetical designation and the precise nature of the therapy (e.g., the designators C and D for cardioversion and DF respectively, are fortuitous).

Figure 2A:
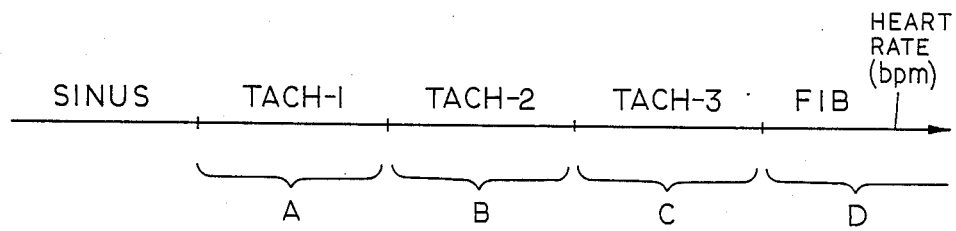
FIGS. 2a and 2b are diagrams illustrating the assignment (prescription) of exemplary therapy regimens to the arrhythmia classes.

Another important feature of the therapy control scheme of the invention is that there is no conceptually pre-defined association between the basic therapies and the designated arrhythmia classes. That is, from a conceptual standpoint any or all of the basic therapies may be prescribed for any of the arrhythmia classes. However, that does not dictate against the physician specifying one therapy per arrhythmia class in the particular order listed above. For instance, as indicated in FIG. 2a, a single extra-stimulus (this and other possible fine structures of the therapies will be described presently) THERAPY-A pacing burst could be prescribed (i.e., programmed) by the physician as suitable treatment to pace the patient out of a very low rate, hemodynamically well tolerated VT detected in region TACH-1; a more aggressive autodecremental pacing burst of THERAPY-B could be prescribed as the appropriate treatment for a higher rate, moderately tolerated VT of class TACH-2; a 2-joule cardioverting shock of THERAPY-C for a poorly tolerated VT in class TACH-3; and a 30-joule defibrillating shock of THERAPY-D in response to detection of VF.

While the association between therapies and arrhythmia classes is intended to be flexible, there are practical considerations that necessarily place certain limitations on the designation of a therapy vis-a-vis a particular class. For example, if VF is to be treated, it follows that a defibrillating shock therapy should be specified for that class of arrhythmia, and that because time is of the essence in treating VF, an aggressive pacing burst is neither a viable alternative nor a suitable preliminary therapy to the defibrillating shock. Despite such practical limitations, the physician is provided with considerable control over the nature and aggressiveness of the therapy regimen to be delivered in response to any given class of arrhythmia, in both the capability to specify the fine structure of each therapy and to combine the therapies in a desired delivery sequence.

A basic principle of therapy control according to the invention is that the therapies delivered by the device should become more aggressive with increasing rate of the tachyarrhythmia and/or with passage of time for a continuing tachyarrhythmia. In the presently preferred embodiment, for any specified combination of the basic therapies applicable to a particular arrhythmia class, the therapies are delivered in the order (sequence) of increasing aggressiveness. An illustration of such therapy sequencing will be described with reference to FIG. 2b. In this instance, the physician has prescribed the combination of THERAPY-A and THERAPY-B for delivery in response to detection of a TACH-1 event (i.e., an arrhythmia in the TACH-1 class); THERAPY-A, THERAPY-B, and THERAPY-C for a TACH-2 event; THERAPY-B and THERAPY-C for a TACH-3 event; and THERAPY-D for a FIB event (VF).

Assuming that the fine structures of these therapies are the same as those specified in the preceding example described with reference to FIG. 2a, these prescribed therapy regimens for the arrhythmia classes are manifested as follows. Upon detecting a class TACH-1 VT, the device will initially apply a single extra-stimulus pacing pulse to the heart via a stimulating cathodic electrode positioned for ventricular stimulation. If that therapy fails to pace the patient out of the tachycardia, the continued presence of the VT will be sensed by a redetection algorithm of the device upon completion of delivery of the therapy. (The redetection algorithms will be described presently.) In response to redetection of the VT, the device will promptly deliver an autodecremental burst of pacing pulses as the second attempt to break the VT. Unless certain therapy control options (to be described below) have been selected by the physician, the sequence THERAPY-A, THERAPY-B will be repeated while the VT remains in progress and in class TACH-1, up to the device's capability for repetitions (255 times in this particular instance, in the present embodiment).

If the VT accelerates to the TACH-2 class, regardless of whether this occurs after delivery of a therapy or while either THERAPY-A or THERAPY-B is in progress, the device will proceed directly into the "default" sequence for TACH-2. The default sequence is the therapy sequence programmed by the physician for that arrhythmia class (in this example, THERAPY-A, followed by THERAPY-B, followed by THERAPY-C), and always follows the rule (in the absence of particular ones of the therapy control options, to be described presently, having been selected) that if the arrhythmia accelerates or decelerates (i) the therapy or therapy sequence for the old class ceases (even if a therapy is in progress at the time of the transition), and (ii) the least aggressive therapy prescribed for the new class is commenced immediately. If two or more therapies have been prescribed for the new arrhythmia class, the therapy sequence is always delivered (again, in the absence of certain therapy control options having been selected) in the order from least aggressive to more aggressive. For the currently preferred embodiment, this scheme results in delivery of the therapy sequence in alphabetical order. It will be observed that in the present example, the default change does not result in an increase in therapy aggressiveness.

Figure 2B:
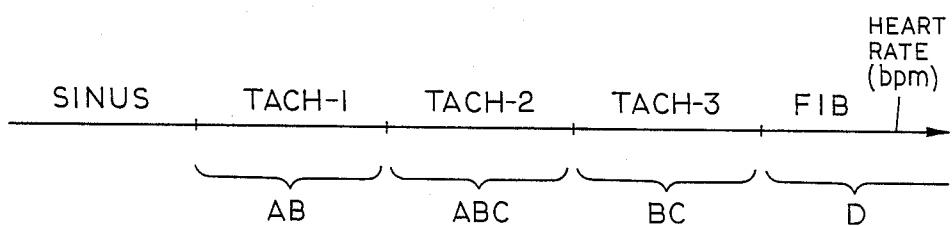

Continuing with the example of FIG. 2b, if the VT had accelerated to TACH-3 during the therapy delivery sequence for TACH-1, that new event will be sensed from application of the redetection algorithm, and the cardiac stimulator will commence the delivery of the therapy sequence prescribed for TACH-3. In that instance, the programming dictates the delivery of THERAPY-B, which could be an autodecremental pacing burst to the stimulating electrode as the first response, and, should that fail to terminate the tachycardia, prompt follow-up with THERAPY-C, which could be a 2-joule cardioverting shock to appropriately positioned electrodes distinct from the pacing electrode and suitable for handling a pulse of that energy level.

If a VT decelerates to a lower class, say, from TACH-3 to TACH-1 in the example of FIG. 2b, the default order will be the delivery sequence THERAPY-A, THERAPY-B. Also, if the VT were to commence at a rate within, say, the TACH-3 region, the therapy control responsive to the detection of that event would be the delivery sequence specified for TACH-3—THERAPY-B followed by THERAPY-C in the case of the present example. It should be emphasized that references throughout this specification to a therapy delivery sequence in response to detection of an arrhythmia, are intended to mean delivery of each therapy in the order of aggressiveness, and repetitions of that sequence, only until the arrhythmia is terminated. That is to say, if a TACH-3 VT is terminated by THERAPY-B in the example of FIG. 2b, that result is detected by the stimulator which thereupon promptly discontinues the therapy regimen so that THERAPY-C will not be delivered.

If the patient has a tendency to accelerate spontaneously from VT to VF the therapy regimen prescribed into the device by the physician for that patient is likely to be more aggressive than the regimen selected for response to detection of an identical tachyarrhythmia in a patient whose cardiac history indicates no such predisposition.

According to another important feature of the invention, the sequence in which the selected therapies are delivered to the patient by the cardiac stimulator may be selectively modified according to a plurality of therapy control options which are programmable by the physician. In the currently preferred embodiment the following options are made available to be exercised by physician programming through the medium of the external programmer unit:

1. Retry exact pacing therapy.
2. Retry last successful pacing therapy.
3. Ratchet.
4. Restart (pacing portion) (1-255).
5. Disable pacing therapies on deceleration limit.

The "retry exact pacing therapy" ("REPT") therapy control option follows the rule that a particular pacing therapy previously delivered in response to detection of an arrhythmia within a specified class is to be redelivered exactly as on the preceding occasion as the first attempt to terminate the arrhythmia, upon the very next detected arrhythmia in that class—but only if that therapy was successful in terminating the arrhythmia on the earlier occasion. Accordingly, if REPT has been selected (programmed) by the physician, the entire last successful pacing therapy sequence delivered for a VT of a given class is stored in memory for the subsequent redelivery.

The "retry last successful pacing therapy" ("RLSPT") option differs from REPT in that RLSPT follows the rule that the precise last pacing therapy in the sequence which was successful in terminating a VT within a particular class, is to be applied as the first therapy upon the very next detected VT within that class. For example, if the RLSPT option has been selected and the therapy sequence successful for the preceding episode was A-B-C, then THERAPY-C will be delivered first on the next detection of an arrhythmia in that class. If either the REPT or the RLSPT option is selected and the respective pacing therapy called for by that option does not succeed in terminating the VT, the treatment will thereupon revert to the prescribed therapy delivery sequence for the particular arrhythmia class.

As noted earlier, programmable and/or stored data features of devices according to the invention are limited only by practical considerations such as available memory capacity. Given sufficient memory, for example, the RLSPT option may be expanded to follow the corollary that the last successful pacing therapy will be redelivered first, and if that fails, the next-to-last successful pacing therapy will be retried, and so forth down the list of prescribed pacing therapies which have succeeded in breaking a VT in the past, for any arrhythmia class to which the physician has assigned a pacing therapy.

The "RATCHET" therapy control option implements the rule that acceleration of a VT to a higher class dictates that the initial therapy delivered for the new class be maintained at least at the level of aggressiveness of the therapy to which the therapy sequence for the old class had progressed. That is, if the RATCHET option is selected, the cardiac stimulator will deliver prescribed therapy for the new class only in the direction of greater aggressiveness of therapy, and not backward from the therapy level reached during treatment in the old class, nothwithstanding that the prescribed therapy sequence for the new class may include one or more less aggressive therapies.

As an illustration of the significance of RATCHET, in the example of FIG. 2b an acceleration of the VT from TACH-1 to TACH-2 at the time THERAPY-B was in progress resulted in a cessation of that therapy and a commencement of THERAPY-A, under the default regimen. This may have been acceptable if little time had elapsed in the delivery of THERAPY-A and through the point of progress of THERAPY-B, up to the moment of acceleration. However, if both of those therapies had been physician-programmed as elaborate scanning bursts, for instance, each might take a clinically significant amount of time to deliver, and in those circumstances it may be desirable to maintain the current level of aggressiveness rather than, as was the case in that example, revert to the less aggressive therapy specified for the new class. If the ratchet option had been selected in that example, upon detection of the acceleration of the VT to TACH-3, treatment would commence with a restart of THERAPY-B from the beginning, rather than a return to THERAPY-A. Further, if the therapy sequence had to be repeated, it would again commence with THERAPY-B.

It will be observed that each of the preceding options tends toward commencing the regimen with a therapy likely to terminate the VT either more rapidly than if the therapy control designated by the option had not been instituted, or with less discomfort to the patient. The underlying premise is that time is of the essence with movement of the arrhythmia toward hemodynamic intolerance, but if greater luxury of time is present (as where the arrhythmia is well tolerated and there is no significant rate advancement) treatment appropriate to arrest the VT without the discomfort attendant in shock therapy may be desirable.

The "RESTART" option is consistent with that premise, providing therapy control in instances when the VT is well tolerated. In essence, RESTART is an appropriate therapy control option where the prescribed therapy sequence begins with one or more pacing therapies and concludes with a shocktype therapy. RESTART calls for a predetermined number of repetitions of the pacing therapy(ies) before proceeding into the shock therapy. Thus, if the therapy sequence specified for delivery in response to a TACH-2 event is ABC, and RESTART has been specified, THERAPY-A and THERAPY-B will be repeated the programmed number of times before THERAPY-C is initiated, up to the point of termination of the tachycardia. Selection of the RESTART option may be made such that the pacing therapies are restarted, or not, depending on the specific arrhythmia class.

Reasons for the physician's selection of the RESTART option may include (1) clinical observation that a VT of the class to be treated is hemodynamically well tolerated by the patient; (2) elapsed time from onset of the episode is therefore not as crucial as in instances of moderate or poor tolerance; (3) there is little or no patient discomfort from the pacing therapies, in contrast to a shock-type therapy; and (4) each application of a shock therapy may (and typically does) consume a considerable amount of energy in comparison to the pacing therapies.

Yet another option which may be selected in the presently preferred embodiment is the disabling of pacing therapies on deceleration limit ("DPTODL"). As noted earlier, treatment of a VT carries a significant risk of acceleration to VF. Of course, if that happens the device will promptly detect the VF and apply DF. It has been observed, however, that the application of a defibrillating shock sometimes causes a deceleration to VT rather than a return to sinus rhythm. Theoretically, this may occur repetitively, with the delivery of pacing therapy upon detection of the reemergent VT resulting in acceleration again to VF, and so forth in a pace-shock, pace-shock loop. DPTODL is adapted to break this loop by disabling the pacing therapies after a preset number of decelerations from VF to VT (preferably on the second occurrence), and proceeding directly to shock therapy.

Until the VT is terminated the stimulator will repeatedly deliver treatment according to the specified therapy delivery sequence for that arrhythmia class, unless and to the extent modified by a selected therapy control option, with continuing redetection during each cardiac cycle according to predetermined criteria (to be described presently). It will be appreciated that the availability of the device's therapy control options provides the physician with a powerful tool to adjust the delivery of the therapies from the prescribed sequence for each class, according to the then-available treatment most likely to succeed under the constraints of time, hemodynamic tolerance, acceleration risk, patient discomfort, and energy capacity existing at the time the arrhythmia is detected.

Although the partitioning of the heart rate spectrum into arrhythmia classes in itself provides a foundation for an arrhythmia detection technique, it is desirable to selectively develop additional information beyond the rate boundaries of these classes in order to more reliably classify the arrhythmia. For example, the device might detect a single cardiac interval in the TACH-3 rate range, but that may simply be attributable to an isolated premature ventricular contraction (PVC), which as noted earlier herein is commonly observed in individuals without heart disease, and not the start of a reentrant VT. Also, a detection scheme based solely on the rate ranges of the designated arrhythmia classes could experience difficulty in distinguishing between a sinus VT and a reentrant VT, which may have a considerable overlap in rates.

The present invention avoids such difficulties and provides a highly reliable arrhythmia detection technique, utilizing in part, in the currently preferred embodiment, essentially the same arrhythmia detection system as that described in the 765,047 application, and in further part certain refinements which will be described presently. That portion of the detection system corresponding to the embodiment described in the 765,047 application, will be set forth briefly herein, purely for the sake of the reader's convenience, but the entire disclosure of that copending application is incorporated herein by reference. Differences employed in the current embodiment will be incorporated into this description.

Because reentrant tachycardias are typically characterized by an abrupt onset (in contradistinction to a gradual ramping up in exercise-induced sinus tachycardias) and a stable high rate (in contradistinction to the rate fluctuation of exercise tachycardias), the following four basic detection criteria form the foundation of an arrhythmia detection system:
(1) high rate ("HR")
(2) sudden onset ("SO")
(3) rate stability ("RS")
(4) sustained high rate ("SHR")

The HR criterion specifies (through physician-programming) a high rate run length of n consecutive intervals at a heart rate exceeding a selected base rate. For example, n may range from 1 to 255 intervals (beats) at a rate exceeding the boundary rate separating the SINUS and TACH-1 classes. Thus, if n is programmed at, say, 6 and the lower boundary rate for TACH-1 is specified to be, say, 100 bpm, the HR criterion is satisfied if the patient's heart rate exceeds 100 bpm over the course of at least 6 consecutive beats.

The SO criterion consists of a physician-specified step increase (delta change) in the heart rate. The SO criterion is satisfied if the patient's heart rate suddenly jumps by an amount exceeding this delta.

The RS criterion consists of two physician-specified factors, one of which is a run length of n consecutive intervals exceeding a selected base rate, and the other of which is a specified rate stability delta. The RS criterion is satisfied if the patient's heart rate exceeds the specified base rate (which typically would be identical to the minimum boundary rate for the TACH-1 region) over n consecutive beats, and that heart rate does not vary by more than the specified delta rate over those n consecutive beats.

The SHR criterion is analogous to the HR criterion except that the specified run lengths differ. In particular, SHR specifies a considerably longer run length n than that used for the HR criterion.

These four basic detection criteria may be combined by Boolean logic into nine tachycardia detection algorithms, as follows (symbolically in parentheses after each statement of the respective algorithm):
1. high rate (HR);
2. high rate and sudden onset (HR AND SO);
3. high rate and sudden onset, or sustained high rate ([HR AND SO] OR SHR);
4. high rate and rate stability (HR AND RS);
5. high rate and rate stability, or sustained high rate ([HR AND RS] OR SHR);
6. high rate and sudden onset and rate stability (HR AND SO AND RS);
7. high rate and sudden onset and rate stability, or sustained high rate ([HR AND SO AND RS] OR SHR);
8. high rate and either sudden onset or rate stability (HR AND [SO OR RS]);
9. high rate and either sudden onset or rate stability, or sustained high rate ({HR AND [SO OR RS]} OR SHR).

Algorithms 6 through 9, each containing the SHR criterion, are utilized because of the possibility that the individual criteria specified by algorithms 2 through 5 may be too stringent for the respective composite algorithm to be satisfied by a reentrant tachycardia. The SHR criterion acts as a "safety valve" to assure that persistent high rate activity will be detected as a reentrant VT by the device.

The arrhythmia detection algorithms are used for the deciding that the detected evidence is sufficient to declare that a reentrant tachycardia is in progress. In essence, these algorithms serve to distinguish between arrhythmias which should be treated by the device and those which should not be treated. As noted above, there may be a rate overlap between a sinus VT and a reentrant VT, particularly at the lower rates, and hence, rate detection alone does not reliably distinguish between the two. At the higher rates, however, the HR criterion alone suffices as a relible indicator of a reentrant tachycardia.

The detection technique used in the currently preferred embodiment of the cardiac stimulator applies the principle that the algorithm stringency should decrease with increasing rate and thus with increasing hemodynamic intolerance of the arrhythmia. In the present embodiment, the physician may specify three different detection algorithms, each for a different tachycardia class. Accordingly, the most stringent detection algorithm of those specified is appropriately assigned to the tachycardia class having the lowest rate range, and the progressively more relaxed detection algorithms are appropriately assigned to the successively higher rate range classes. It follows that if a highly stringent detection test applied to the TACH-1 region results in inconclusive evidence as to whether a reentrant tachycardia is in progress, and a moderately stringent test applied to the TACH-2 region is satisfied, the evidence is compelling that a reentrant VT is indeed in progress.

Figure 3A:
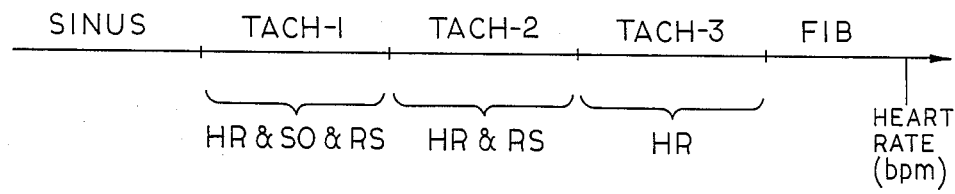
FIGS. 3a and 3b are diagrams illustrating the designation of detection criteria algorithms to the arrhythmia classes.

By way of example, FIG. 3a illustrates a suitable selection of detection algorithms for the tachycardia classes TACH-1, TACH-2, and TACH-3 of FIG. 1a. The most stringent of the algorithms depicted in FIG. 3a, HR AND SO AND RS, is assigned to the TACH-1 region; the most relaxed test, HR, is assigned to the TACH-3 region; and a moderate test intermediate the other two, HR AND RS, suffices for and is assigned to the TACH-2 region.

Provisions are made for reducing the number of detection criteria to be used in redetection following initial screening of the VT, because of the need to deliver the next therapy as quickly as possible if the VT is still in progress and also because less stringent detection criteria will provide suitably compelling evidence. In particular, if any criterion is no longer applicable as a result of the continuation of the initially detected arrhythmia episode, that criterion is discarded from use in redetection, so long as that episode is still in progress. For example, the SO criterion is not viable after initial detection of a VT inasmuch as the episode has now been detected and sudden onset no longer applies. Hence, that criterion is eliminated during any attempted redetection of the progress of that VT. Similarly, the SHR criterion is of no value for purposes of redetection, once having identified a VT in progress. This eliminates algorithms 2, 3, and 5 through 9, inclusive, on the above list from use for purposes of redetection.

High rate (algorithm 1), and high rate and rate stability (algorithm 4), are the only remaining tests suitable for redetection criteria; and since each of HR and RS is useful in both initial screening and redetection, each is assigned two separately programmable n's, namely ni (for initial detection) and nr (for redetection). The reason for the separately selective variables is that, for HR, although a rather long run of consecutive high rate intervals (ni) may be deemed by the physician as necessary for a reliable initial detection of a VT, a relatively shorter run length (nr) will suffice for purposes of redetection. Similarly, for RS, a shorter run of consecutive high rate intervals (nr) of relatively invariant rate may be deemed suitable for redetection, compared to the run length (ni) used for the initial screening.

Figure 3B:
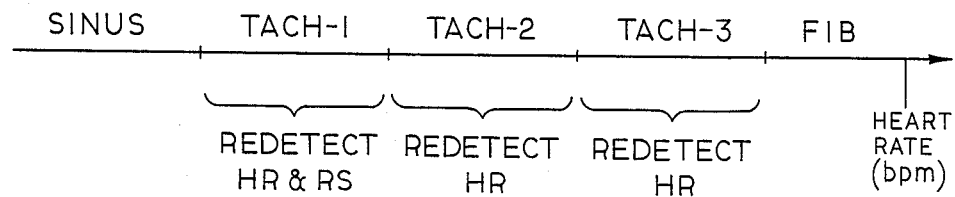

As with the initial screening algorithms, the physician may specify a different redetection algorithm for each of the VT classes. In the scheme illustrated in FIG. 3b, the more stringent redetection algorithm HR AND RS is assigned to class TACH-1, and the more relaxed redetection test HR is assigned to each of the TACH-2 and TACH-3 classes.

A different redetection criterion that may be selected in the present embodiment of the invention is referred to as "HYSTERESIS". Redetections at or near the boundary between adjacent arrhythmia classes may be inconclusive as to whether an acceleration of the arrhythmia has taken place to the next higher class, merely because of minor timing shifts. The "HYSTERESIS" redetection option assigns a rate "delta" which is automatically added to the detected tachycardia rate. If, on redetection under the "HYSTERESIS" option, the redetected rate is below the boundary rate between the two classes, the redetection is conclusive that no acceleration has occurred. Similarly, if the redetected rate is above that boundary rate but still below the initially detected rate plus the hysteresis delta, there is no acceleration. However, if the redetected rate is both above that boundary rate and the initially detected rate plus the delta, an acceleration to the higher class is declared. Hence, the "HYSTERESIS" option is an important feature of the invention for distinguishing accelerations from non-accelerations for arrhythmias which are redetected at rates only slightly above a designated boundary between classes.

According to a further aspect of the present invention, a different set of basic criteria, numbering two in the presently preferred embodiment, is provided for purposes of detecting fibrillation. One of the two is termed fibrillation rate ("FR"), and is somewhat analogous to the HR criterion for tachycardia detection. However, for the FR criterion to be satisfied, a physician-specified run length of n consecutive intervals must occur at a heart rate exceeding the rate at the upper boundary of the highest VT region of the rate continuum (e.g., a rate higher than the TACH-3 range, in the illustrative rate range partitioning of FIG. 1b).

The second basic criterion employed for detection of fibrillation is termed "F x/y". The F x/y criterion specifies that x fibrillation rate intervals must occur within y consecutive intervals (where both x and y are physician-programmable), as indication of VF. The latter criterion serves to detect VF despite the erratic heart rate and widely variable signal amplitude which are characteristic of that arrhythmia. The varying signal amplitude may result in failure to detect some signal peaks, which might falsely appear to be a VT or periods of sinus rhythm under the FR criterion, owing to restart of the count toward n. The F x/y criterion will recognize, in those circumstances, that x fib rate intervals have occurred within the y consecutive intervals.

It is possible that an erratic, high rate cardiac arrhythmia may go undetected if the rates of the individual cycles swing back and forth between the TACH-3 and FIB regions. That is, the arrhythmia could exhibit a few fibrillation intervals which would reset the VT high rate run counter, but insufficient to trigger the FR or F x/y detection criteria. Next, the erratic arrhythmia could exhibit a few TACH-3 intervals which would reset the FR rate counter and count as non-fibrillation intervals in the F x/y criterion. This situation could persist for an extended time, resulting in failure to detect a hemodynamically compromising arrhythmia.

To insure that such an erratic, high rate, hemodynamically compromising arrhythmia is rapidly detected, and to bias the detection in favor of VF and away from a TACH-3 VT, the following additional rules may be applied to the VT and VF detection criteria:

(1) a cardiac cycle in the TACH-3 region is completely disregarded by the FR and fib x/y criteria.
(2) if the high rate count is greater than 0, and a cardiac cycle is in the FIB region, then 1 is subtracted from the high rate counter.

The first rule declares that a cardiac cycle in the TACH-3 region cannot be used as evidence either for or against the detection of VF. The second rule states that an interval in the FIB region offers some (but inconclusive) evidence that a reentrant tachycardia is not in progress.

With these two additional rules in effect, when the erratic rate swings into the TACH-3 class, the detection criteria for VF are unperturbed. Then when the rate swings back into the FIB region, the VF detection criteria pick up as if there had been no intervening TACH-3 interval, allowing VF to be detected. While the rate is in the FIB region, the high rate counter is also being counted down, which tends to suppress the detection of TACH-3 when the rate swings back into that region. Therefore, the detection of VF is enhanced and the detection of a TACH-3 event is suppressed.

The two basic fibrillation detection criteria may be combined by Boolean logic into three VF detection algorithms as follows (symbolically in parentheses following each respective statement of the algorithm):
1. fibrillation rate (FR)
2. fibrillation x out of y (F x/y)
3. fibrillation rate or fibrillation x out of y (FR OR F x/y)

The foregoing algorithms provide multiple detection criteria for the region of the heart rate continuum exceeding the upper boundary of the highest tachycardia class.

After detection of an arrhythmia in one of the TACH or FIB classes, and in response, the delivery of the prescribed therapy sequence (modified by any selected therapy control option), the implanted stimulator must assess whether sinus rhythm has been reestablished. The anti-tachycardia pacemaker embodiment described in the 765,047 application uses a single long interval as the determinant for redetection of sinus rhythm. While that is a generally satisfactory technique, it has been found that on some occasions following therapy a single long interval criterion may give a false indication of reestablishment of sinus rate.

According to the present invention, a more effective criterion of reversion to sinus rate specifies that there must be x intervals at sinus rhythm out of any y consecutive intervals. Both x and y are physician-programmable. The sinus x out of y basic criterion ("sinus x/y") is also the only algorithm used for the purpose of this detection. It is preferable that relatively long counts be used for the programming of x and y; for example, the physician might set x at 18 and y at 20. The reason for this is that there is no clinical harm in a slight delay to provide a more reliable indicator of reversion to sinus rhythm, in contrast to the undesirability of delaying detection of a VT (particularly one that is poorly tolerated hemodynamically by the patient), or of VF.

Returning now to the therapy aspects of the present invention, an overall philosophy incorporated into the presently preferred embodiment is to provide the physician with virtually complete control over the aggressiveness of the therapy, within the availability of programmable individual therapies and therapy regimens. Consistent with that philosophy, each of the therapies is provided with a selectively modifiable fine structure, as previously mentioned, to permit the physician to even more closely adapt the treatment afforded by the stimulator to the needs of the patient.

In the presently preferred embodiment, included among the fine structures that may be prescribed by the physician for the shock-type therapies, are:
(1) number of shocks to be delivered (i.e., the number of attempts to terminate the detected arrhythmia);
(2) sense-to-shock delay (in milliseconds), to time the delivery of the shock relative to a particular portion of the ECG waveform (such as for synchronizing cardioverting shocks with that portion most likely to result in rapid termination of the tachycardia, while avoiding the vulnerable period);
(3) amplitude of shocking pulses for first attempt, and amplitude for subsequent attempts to terminate the arrhythmia (e.g., specifying a low level on the first attempt, and a relatively higher level if subsequent attempts are necessary, in keeping with increasing the aggressiveness of the therapy);
(4) definition of the waveform of the shock applied to the heart (e.g., specifying up to six phases including pulse width, polarity, and presence (i.e., on) or absence (i.e., off). For example, the waveform could be specified as a tri-phasic waveform with a positive pulse, a negative pulse and another positive pulse; or a sequence of two pulses separated by a gap as by specifying a negative pulse for a first pulse width, no pulse for a second pulse width, and a negative pulse for a third pulse width, and so forth). A detailed description of multiphasic waveforms is set forth in the copending U.S. patent application Ser. No. 847,283, of William Winstrom, filed Apr. 2, 1986, entitled "Apparatus for Generating Biphasic Defibrillation Pulse Waveform", and assigned to the same assignee as is the present application.

Referring now to the pacing therapies, and once again to the 765,047 application, an embodiment of the invention described therein is adapted to terminate detected atrial reentrant tachycardias with a properly timed burst of stimulation pulses. In that embodiment, the number of attempts is programmable, and a burst may be programmed with respect to number of pulses in the burst, sense-to-initial pulse delay interval, and burst cycle length (i.e., the pulse-to-pulse interval).

Further, that embodiment allows both the initial delay interval and initial burst cycle length to be programmed with fixed values, or with adaptive values as a percentage of the interval between tachycardia beats; and to be changed in a scanning mode in which the values of those parameters or of either of them are decremented, or alternately incremented and decremented, over successive bursts after the initial burst (the "burst scanning" mode). The physician may also select a mode in which the interval between consecutive pulses in a burst is automatically decremented (hence, termed "auto-decremental" mode). The burst scanning mode is also programmable with respect to three parameters, namely, step size (i.e., amount by which value of delay interval and/or burst cycle length is increased or decreased for each successive burst), number of steps (i.e., number of times those values will be incresed or decreased by the selected step size), and number of sequences (i.e., number of times a scan sequence is to be repeated).

The current preferred embodiment of the present invention utilizes and provides the fine structure capabilities of the 765,047 application, as well as certain improvements in physician-programmable fine structures for the pacing therapies, as follows:
1. number of attempts (1-255);
2. decremental (DEC) or search (SEARCH) scan;
3. coupling delay/fixed or adaptive;
4. S1 burst cycle length (BCL)/fixed or adaptive; and S1 number of pulses (0-255);
5. S2 BCL/fixed or adaptive; and S2 number of pulses (0-255);
6. S3 BCL/fixed or adaptive; and S3 number of pulses (0-255);
7. S4 BCL/fixed or adaptive; and S4 number of pulses (0-255);
8. scanning step for coupling delay/fixed or adaptive;
9. scanning step for S1 BCL/fixed or adaptive;
10. scanning step for S2, S3, S4 BCLs/fixed or adaptive;
11. auto-decremental (AUTO-DEC) step for S1, S2, S3, S4 BCL/fixed or adaptive;
12. minimum interval/fixed or adaptive;
13. number of steps to scan (0-255);
14. add S1 pulse per attempt.

In the foregoing list of programmable fine stuctures for the therapies, the number of attempts refers to attempts to terminate a VT in any TACH class in which the pacing therapy is applied. The fine structure of the system's burst pacing therapies provides two kinds of scanning behavior—(1) decremental scan which starts with the initial burst definition and in which intervals become progressively shorter by the selected step amount; and (2) search scan which similarly starts with the initial burst definition and in which the intervals become progressively longer and shorter as they are alternately incremented and decremented in a search for the termination zone of the tachycardia in the ECG.

Figure 4:
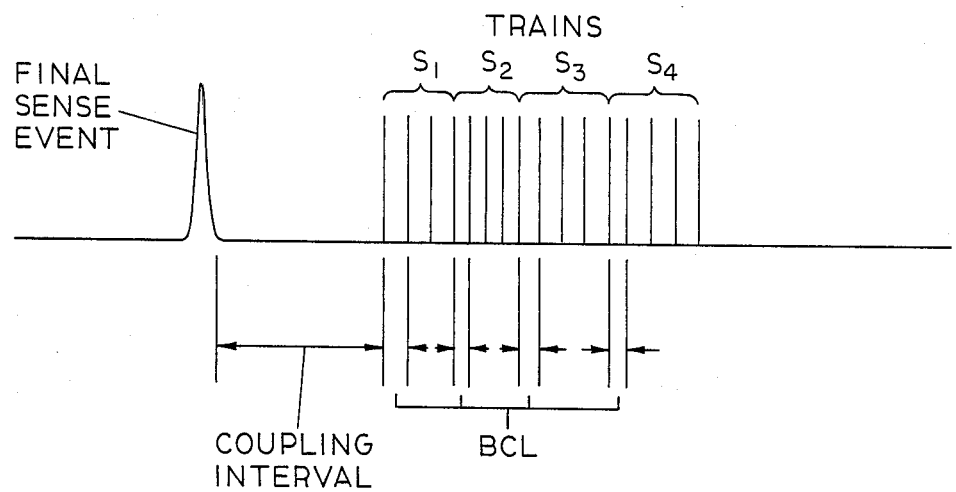
FIG. 4 is a diagram indicating the characteristics of the fine structure of the burst pacing therapies.

Referring to FIG. 4, the coupling interval is the time interval between last detection of the tachycardia (sense event) and delivery of the first pulse in the burst. The first pulse train in each scan is termed S1, and sequential pulses in that train are separated by identical time intervals referred to as the S1 burst cycle length (BCL). Thus, S1 BCL is the pulse-to-pulse interval for train S1. The BCL may be physician-specified either as a fixed time interval or as an adaptive percentage of the measured tachycardia rate, and the number of pulses in the S1 train may be separately specified. Further, the physician may specify three additional stimuli in each scan, these being the successive pulse trains S2, S3 and S4 following the S1 train. As in the case of S1, the BCL (which will differ for each train) in either fixed or adaptive mode, and the number of pulses, may be programmed for each of S2, S3 and S4. The combination of the coupling interval and the succession of pulse trains following any given sense event is the entire burst.

Still further, separate scanning steps may be specified for each parameter within a burst, that is, for the coupling interval and the BCL for each of the pulse trains; and the coupling delay and, for any given train within the burst, the BCL may be selectively fixed or adaptive. If an auto-decremental step is selected, the BCL in each of the trains within the burst to which that selection applies becomes progressively shorter (by a fixed or an adaptive amount, as specified by the physician at the time of programming the device) when and as the therapy is delivered. In addition, the present embodiment allows auto-decremental burst to be programmed for scanning (i.e., the burst may be scanned as it or selected parameters are decremented).

For the sake of clarity, scanning will be described with reference to an exemplary burst. In the case of decremental scanning the originally specified burst is delivered to the heart, and if that fails to terminate the tachycardia, the BCL of successive pulses (and coupling interval, if so programmed) in the next burst delivered is automatically decreased by the specified step amount, i.e., the pulses are closer together in the next burst. Successive bursts are similarly decremented relative to the immediately preceding burst by the designated step for the selected parameters, until successful arrest of the tachycardia or completion of the treatment sequence.

In the case of search scanning, if the first attempt (burst) is unsuccessful, the next burst is delivered with a longer BCL and/or coupling interval (depending upon the specific parameter programming) by the specified step amount. Subsequent bursts, up to the point of successful termination or of completion of the treatment sequence, are alternately shorter and longer in the specified parameter(s) by the step amount, e.g., the next longer BCL burst has a time interval between pulses which is greater by the step amount than that interval in the immediately preceding longer BCL burst (those two bursts being separated by a shorter BCL burst in the alternation cycle). However, in the case of auto-decrementing the BCL is decreased by the specified step amount for each pulse in a single burst.

The minimum interval sets a lower limit on the scanning, and on the step reductions; hence, that interval defines completion of the treatment sequence. When the BCL reaches 50% of the time interval between beats of the VT, the risk becomes considerably greater that the VT will be accelerated to VF. Accordingly, it is desirable to set the minimum interval to remain safely above that critical level as determined for the particular patient for whom the device is to be used. By appropriate selection of the number of steps to scan, coupled with setting of the minimum interval, the aggressiveness of the treatment is selectively adjusted.

In further keeping with the methodology and design philosophy of providing the physician with maximum control over aggressiveness of the therapy and over the degree by which that aggressiveness is incrementally increased, the capability is also provided to add a single pulse to the S1 train in each burst. The premise here is that if the preceding burst was unsuccessful, the next attempt should be at least slightly more aggressive; and the more pulses in the train the more aggressive the therapy.

Figure 5:
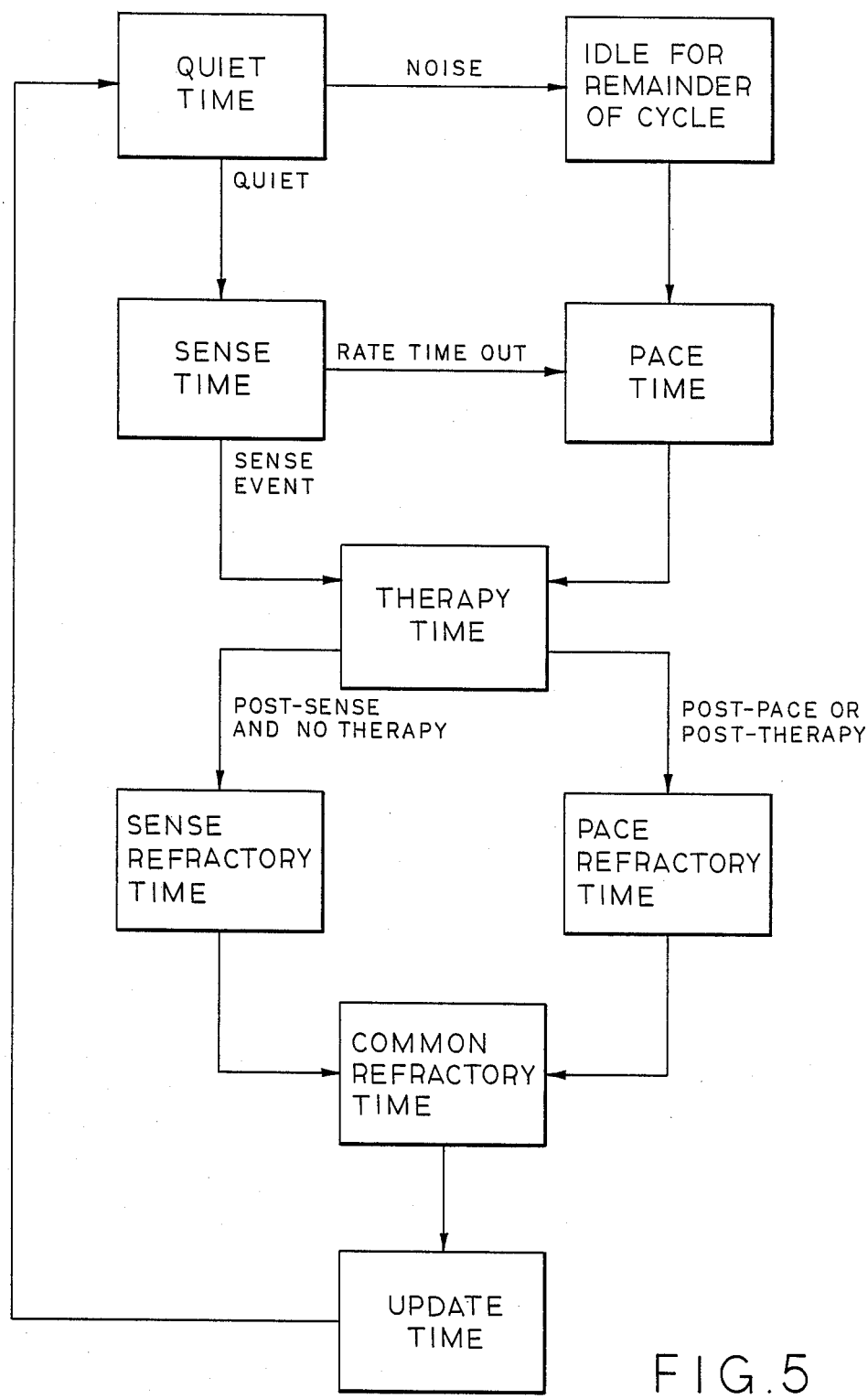
FIG. 5 is a flow diagram illustrating timing aspects of the cardiac stimulator.

The timing of the sensing, arrhythmia detection, therapy preparation and therapy delivery is illustrated for each cardiac cycle by the flow diagram of FIG. 5.

Quiet time: Monitor input leads for high frequency noise. If noise is detected, then go to idle time. If no noise is detected, go to sense time.

Sense time: Wait until a cardiac event is sensed, or until it has been longer than the bradycardia interval since the last sensed or paced cardiac event. Record the length of the cardiac cycle and save it. If a cardiac event was sensed, then go to therapy time; otherwise go to bradycardia pace time.

Idle time: Note that noise was sensed, then wait until it has been longer than the bradycardia interval since the last sensed or paced event. Go to brady pace time.

Brady pace time: If appropriate based on selected mode, generate a pacing pulse.

Therapy time: If a therapy was set up during common refractory time in the previous cycle, then deliver it now. If a therapy was delivered or a brady pacing pulse was emitted this cycle, then go to pace refractory time; otherwise go to sense refractory time.

Sense refractory time: Update diagnostic counters associated with a sense event. Go to common refractory time.

Pace refractory time: Wait until the beginning of the T-wave window. Go to common refractory time.

Common refractory time: Use the interval just measured to update the arrhythmia and sinus detection criteria and algorithms. If an arrhythmia is detected or redetected, prepare the appropriate therapy to be delivered synchronously during the next therapy time. Wait until either the sense refractory time or the end of the T-wave window. Go to update time.

Update time: Based on the sensing/pacing history of the cycle up to this point, update the automatic gain control system. Perform miscellaneous initialization chores for the next cycle. Go to quiet time.

In the foregoing flow sequence, if an arrhythmia is detected in the previous cycle, then the therapy is delivered in the current cycle, regardless of whether noise or a rate timeout was experienced.

External control of certain physician-designated functions may be given to the patient for selection by means of a magnet to be used in conjunction with a reed switch within the implanted cardiac stimulator. Any such functions will only be magnet-accessible to the patient if so programmed by the physician. One aspect of magnet control typically made available to the patient in implanted pacemakers, and appropriate to be made available to the patient in the present embodiment, is that related to transtelephonic monitoring of various functions or characteristics of the implanted device.

In the stimulator of the invention, an elective replacement indicator (ERI), an end-of-service indicator (EOS), and enabling of a capture verification test (i.e., to assure that pacing stimuli are producing the desired response in the excitable cardiac tissue), are among the functions which may be magnet controlled by the patient, for purposes of transtelephonic monitoring of the device. The ERI/EOS/capture verification tests available in the device are:

1. Low battery detected by the ERI comparator (this comparator detection is ignored by the microprocessor for a period of several hours after charging of the capacitors, during which the indication may be erroneous).
2. Post-charge battery voltage below preset limit.
3. During high voltage charge-up, microprocessor-requested voltage level not reached within a specified short interval (e.g., 30 seconds), indicating low battery.
4. Total charging time for all shocks exceeded a preset limit.

The ERI/EOS and capture tests are performed by the device as follows:

1. If the magnet is applied and ERI/EOS is not detected, the device will generate a total of 13 pacing pulses in the VVI mode at a rate of 100 pulses per minute (ppm), with the last pulse width halved for purposes of the capture test.
2. If the magnet is applied and ERI/EOS is detected, the device will generate a total of 5 pacing pulses in the VVI mode at a rate of 100 ppm, with the last pulse width halved for capture test.

Other potential magnet functions available in the preferred embodiment, which are mutually exclusive, are:

1. Perform none of the other functions in this category.
2. Inhibit detection of arrhythmias and delivery of therapies.
3. Enable detection of arrhythmias and delivery of therapies.
4. Reduce tachycardia detection and redetection algorithms to "high rate" only.
5. Cause delivery of one of the four therapies; the selected therapy being programmable. If a scanning burst is selected, the first burst in the scan will be delivered. For a shock, first energy will be delivered.

The presently preferred embodiment of the cardiac stimulator is structured to be implanted in the patient. A unit including the portion of the stimulator for detecting and distinguishing the significance of the patient's cardiac activity, and responsive to abnormal arrhythmias for generating and managing the delivery of pacing and shock therapies, with self-contained power source, may be assembled and housed in a metal case inert to body tissue and fluids. That unit is sometimes referred to herein as a "multiple cardiac therapy generator", or more simply as the "therapy generator" (although it will be recognized that its functions go beyond mere therapy generation), and in that respect is somewhat akin to the pulse generator unit of a cardiac pacemaker. Lead/electrode assemblies for sensing cardiac activity and for delivering the respective pacing and shock impulses to the patient's heart may be separably connectable to the therapy generator, and in that respect are somewhat akin to the leads of a cardiac pacemaker. Together, the therapy generator and the lead/electrode assemblies constitute the cardiac stimulator.

The therapy generator includes a digital control section for storing and executing software instructions and for storing and processing the data for all digital functions of the device (aside from those functions which, for purposes of conserving memory capacity, are readily consigned to an external programmer unit ("programmer") of conventional type available to the physician). The digital functions of the device include the previously described physician-programmable aspects, such as provision for programming the rate boundaries of the VT (TACH) classes to selectively partition the rate continuum, the therapies (including gross and fine structures) and therapy delivery sequences, and the detection and redetection algorithms, as well as various processing, timing, switching, control and other functions to be described presently.

The therapy generator also includes an analog portion for such functions as monitoring the patient's ECG signal information over each cardiac cycle, enhancing that signal information while eliminating noise and other interference through signal filtering and automatic gain control, developing the respective impulse waveforms to be delivered for the pacing and shock therapies, transmitting data between the device and external units such as the programmer and transtelephonic monitoring equipment, and protecting against overloads, at least some of these analog functions being controlled according to the programmed instructions.

Also included within the therapy generator are the battery cells, and voltage regulation and priority power sequencing section, for supplying power to the other sections of the overall generator.

Figure 6:
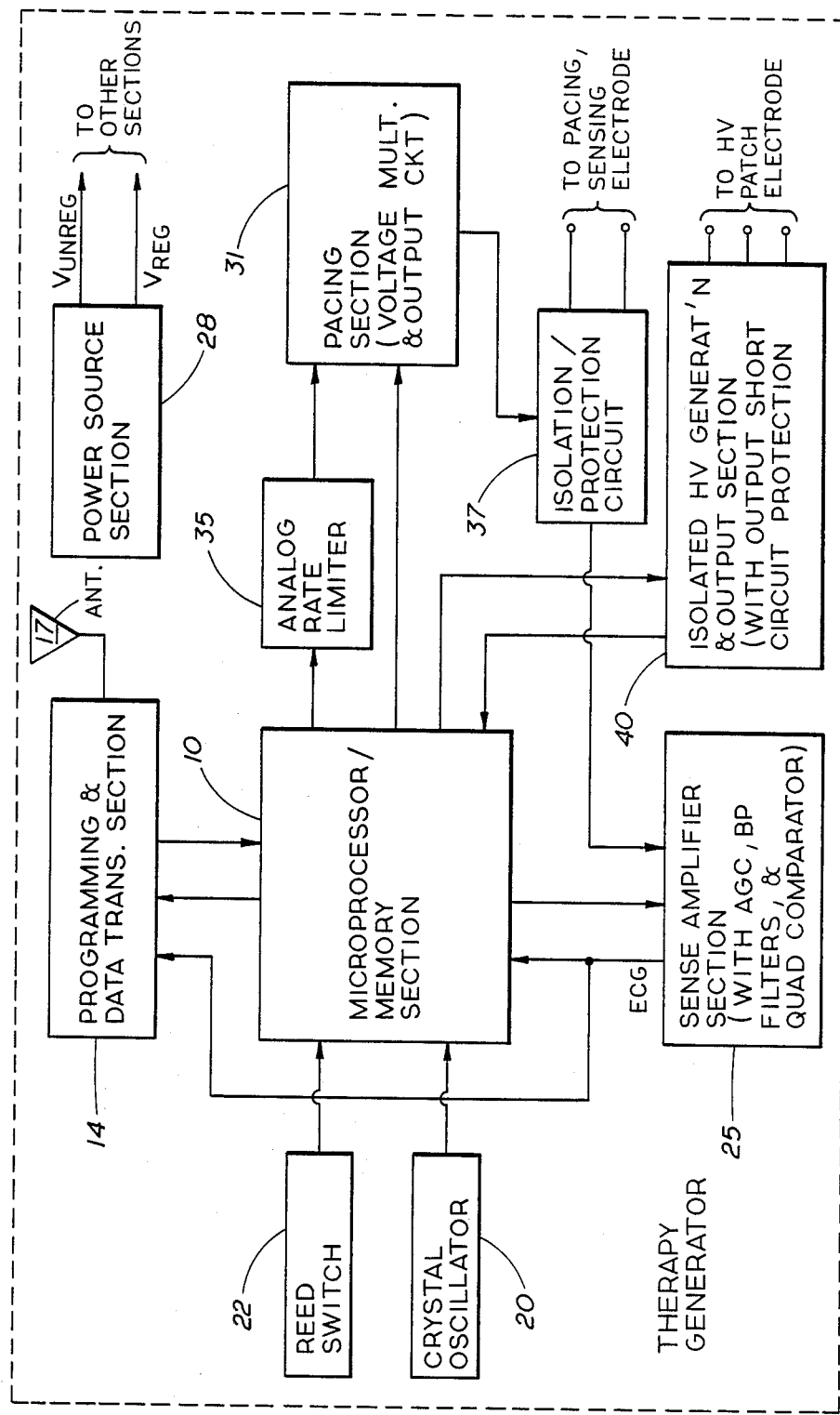
FIG. 6 is a diagrammatic representation of the electrical circuit of a presently preferred embodiment of the implantable cardiac stimulator according to the invention.

The electrical circuit configuration of a present embodiment of the overall cardiac stimulator will now be described by reference to the remaining FIGS. of the drawing. With initial reference to FIG. 6, the therapy generator includes a section 10 comprising a central microprocessor with associated memory capacity including random access memory (RAM) and read only memory (ROM), for processing and storing data necessary to provide the features described earlier herein. The microprocessor and memory circuits are preferably complemetary metal-oxide-semiconductor (CMOS) integrated circuit chips for low voltage, low power operation. Section 10 is bidirectionally coupled to a programming and data transmission section 14 which serves to transmit data to receiving and monitoring equipment (e.g., transtelephonically) for analysis and assessment of the cardiac functions of the patient and the operating condition of the implanted device, and for receiving program instructions and data from the external programmer, all via an implanted antenna 17.

A crystal oscillator 20 electrically coupled to section 10 provides the necessary precise timing signals for system operation. A reed switch 22 is also electrically connected to section 10 to permit limited external control by the patient of certain programmable functions, such as those previously described, by using an external magnet to control actuation of the switch.

A sense amplifier section 25, which includes automatic gain control and bandpass filtering, is coupled to section 10 for transmitting ECG signal information to the microprocessor and for receiving control signals from the microprocessor. The sense amplifier is also connected to data transmission section 14 so that the ECG telemetry signal information may be supplied via the latter to external monitoring equipment. A quad comparator within section 25 provides the link for converting the ECG sense signal information obtained from the sensing electrode(s) and processed by the sense amplifier into digital information suitable for use by the microprocessor. The microprocessor is within a feedback loop of the sense amplifier to provide improved automatic gain control, as will be explained in greater detail below.

The sense amplifier enhances the ECG signals to aid the tracking of signal content of rapidly varying amplitude, such as fibrillation signals. Preferably, the sense amplifier has a gain range on the order of 60:1. In addition, bandpass filtering is employed to provide the dual function of (1) reducing the amplitude of signals outside the frequency band of interest and (2) further amplifying the low frequency (e.g., fibrillation) signals within that band in the absence of normal R-waves.

The power source section 28 of the overall stimulator system comprises high rate battery cells, a voltage regulator and a priority power sequencer. The high rate cells comprise any combination of cells capable of delivering sufficient energy to charge the capacitors in the output high voltage section (40) within a reasonable time (e.g., 20 seconds or less). The voltage regulator circuit has a voltage divider to provide a 3:1 reduction if three cells are used in series, as is preferred, or a 2:1 reduction if only two cells are employed, and thereby improves power source efficiency. The priority power sequencer is used to assure adequate power is made available to the essential circuit functions such as the control logic during periods when there would otherwise be high current drain on the cells, such as during charge up of the high voltage capacitors in preparation for the delivery the defibrillating or cardioverting shock therapies.

The pacing section 31 of the system includes a voltage multiplier and output section, the former serving to scale up the regulated supply voltage from power source section 28 by multiples of one, two or three. The output section provides the output switching from this scaled voltage to deliver the pacing stimuli to the patient's heart via the pacemaker circuit including cathodic stimulating and anodic reference electrodes, under the control of the microprocessor.

An analog rate limit circuit 35 between microprocessor/memory section 10 and pacing section 31 is employed to controllably limit the pacing rate, and thereby safeguard against pacemaker runaway, in the event of failure of the crystal oscillator circuit. However, the rate limiter is automatically disabled whenever an intentionally high rate of pacing pulses is required, such as during the generation of a burst pacing therapy.

The leads for the pacing and sensing electrodes are electrically monitored by the isolation/protection section 37. The latter functions to protect low voltage, low power components of the stimulator from the high voltage of the defibrillating shocks generated by the stimulator (or applied from an external defibrillator that may be used on the patient during emergency medical procedures). One suitable protection circuit is disclosed in the copending U.S. patent application Ser. No. 799,804, of William Winstrom, entitled "Protection Apparatus for Patient-Implantable Device", filed Nov. 20, 1985, and assigned to the same assignee as is the present application.

The cardioverter/defibrillator shock therapy portion of the stimulator includes an isolated high voltage generator and output section 40. The voltage generator circuitry includes a high voltage oscillator coupled via an isolation transformer to output capacitors for charging the capacitors to the required voltage levels for the cardioverting and defibrillating shocking pulses, under the control of the microprocessor.

A low power analog-to-digital (A/D) converter in section 40 is utilized to monitor the voltage on the capacitors, to permit the microprocessor to set the desired high voltage output level in accordance with the physician-programmed fine structure energy content of the applicable shock therapy. Monitoring of the capacitor voltage also allows the microprocessor to measure the residual charge on the capacitors after delivery of each output pulse, and thereby to estimate the amount of energy consumed in the delivery for ongoing assessment of remaining capacity of the battery cells. In addition, the A/D converter input circuit may be switched by the microprocessor for connection to the power source section 28 to monitor the battery voltage, and thereby determine the present condition of the cells.

Output section 40 also contains level shifters and isolation transformers to convert the microprocessor-supplied low level logic control signals to the control signal levels required to drive the output switches of that section. The output switches themselves are of low "on" impedance and capable of handling the high voltages and currents being generated, to control the delivery and polarity of each output pulse. A short circuit protection circuit is provided in output section 40 to open the output circuit in the event that the current through that circuit rises above a predetermined level. This prevents a discharge of the capacitors into a very low impedance—such as if the defibrillator patch electrodes were shorted—and thereby protects the output switches from overstress and potential destruction.

Figure 7:
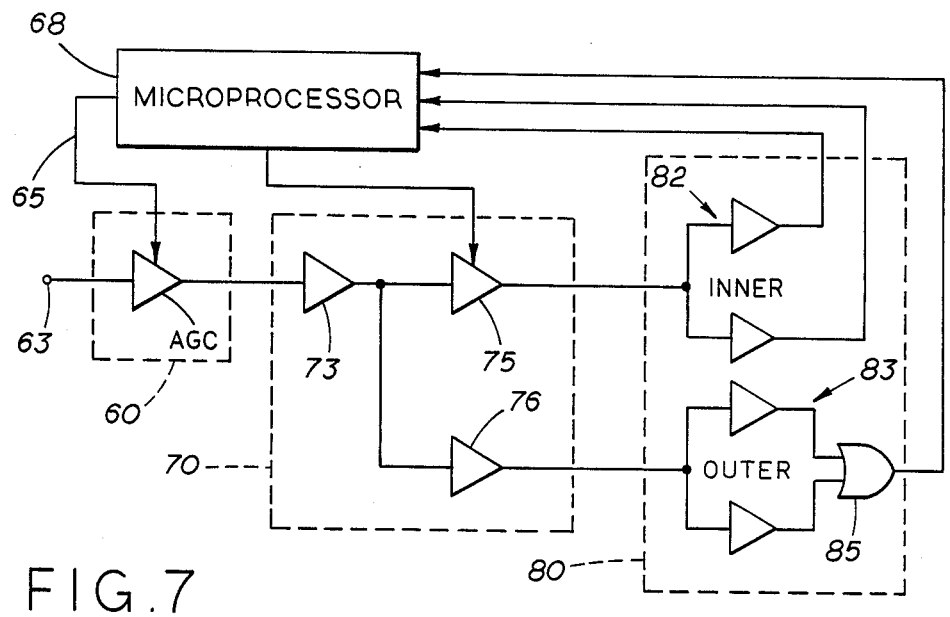
FIG. 7 is a more detailed diagram of a portion of the circuit of FIG. 6.

The sense amplifier with AGC and related bandpass filtering and quad comparator, and including the relationship with the microprocessor, is shown in somewhat greater detail in FIG. 7. The sensed ECG waveform components detected by the sensing electrode(s) are applied to the sense amplifier 60 via an input circuit 63. The gain of the sense amplifier is automatically controlled by a feedback loop 65 which includes the microprocessor 68 of section 10.

The ECG signals processed by the sense amplifier are additionally enhanced by a filtering section 70 which includes a primary high gain bandpass amplifier 73 to reduce signal strength outside the selected band and to amplify low frequency signals within the band. The output of amplifier 73 is split and fed into separate bandpass amplifiers 75, 76, one of which (75) is digitally controlled by the microprocessor. The output of the gain/filtering control stages is applied to the quad comparator 80, which develops three inputs to the microprocessor in the feedback loop.

The AGC system of the presently preferred embodiment deals effectively with the difficult problem of sensing the low frequency, low signal amplitude characteristic of VF. Under ordinary circumstances, a loss of sensing may be indicative of VF, requiring that the gain of the sense amplifier be increased to enable better detection. However, if the loss of sensing is attributable to an intermittent heart block rather than fibrillation, a return of sense signal is likely to be overamplified with a consequent serious perturbation of the entire system. The manner in which the AGC system resolves this problem will be explained presently, in connection with the description of FIGS. 10 and 11.

Figure 9:
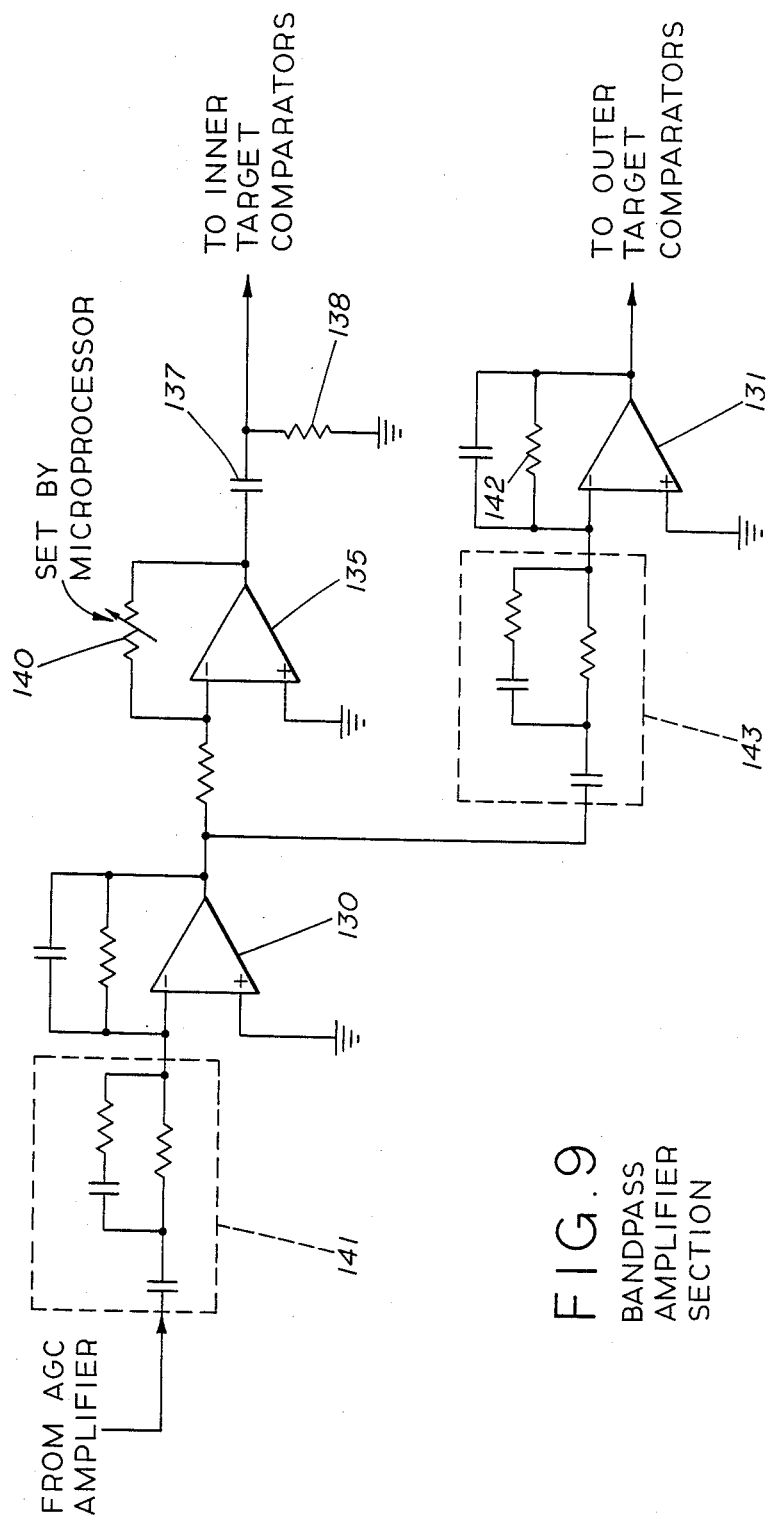
Figure 10:
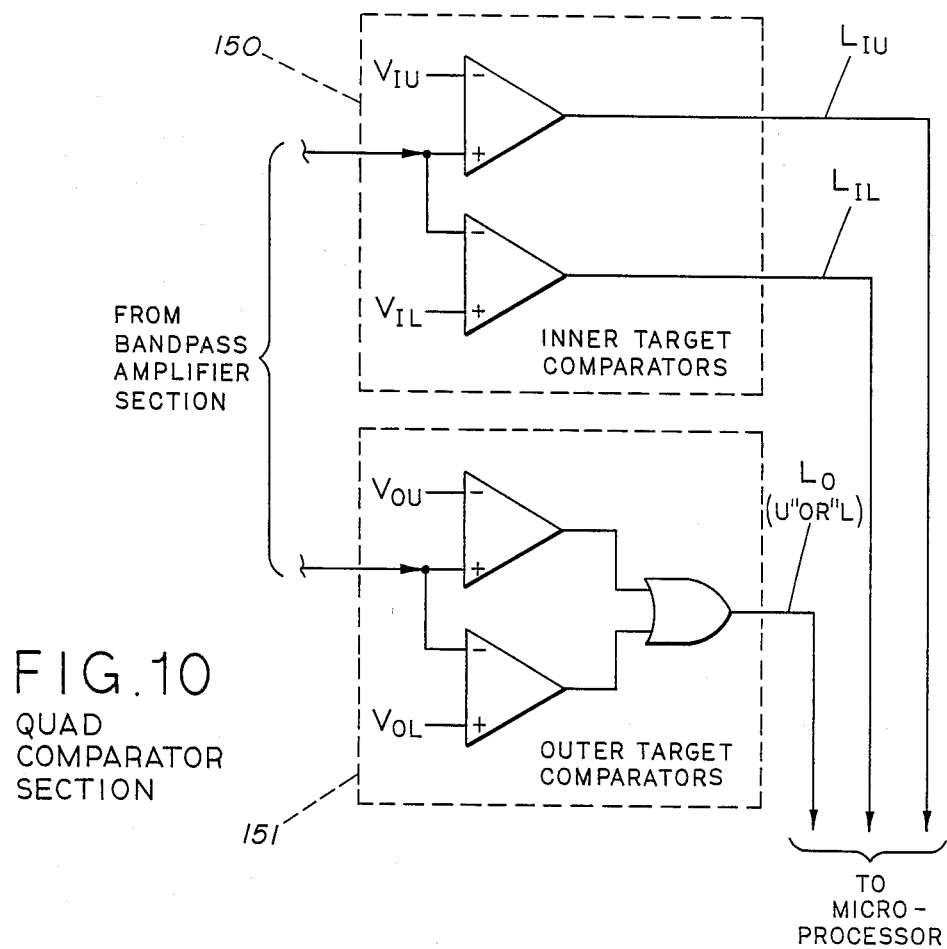

Sense amplifier section 25 comprises an AGC amplifier section (FIG. 8), a bandpass amplifier section (FIG. 9), and a quad comparator section (FIG. 10).

Figure 8:
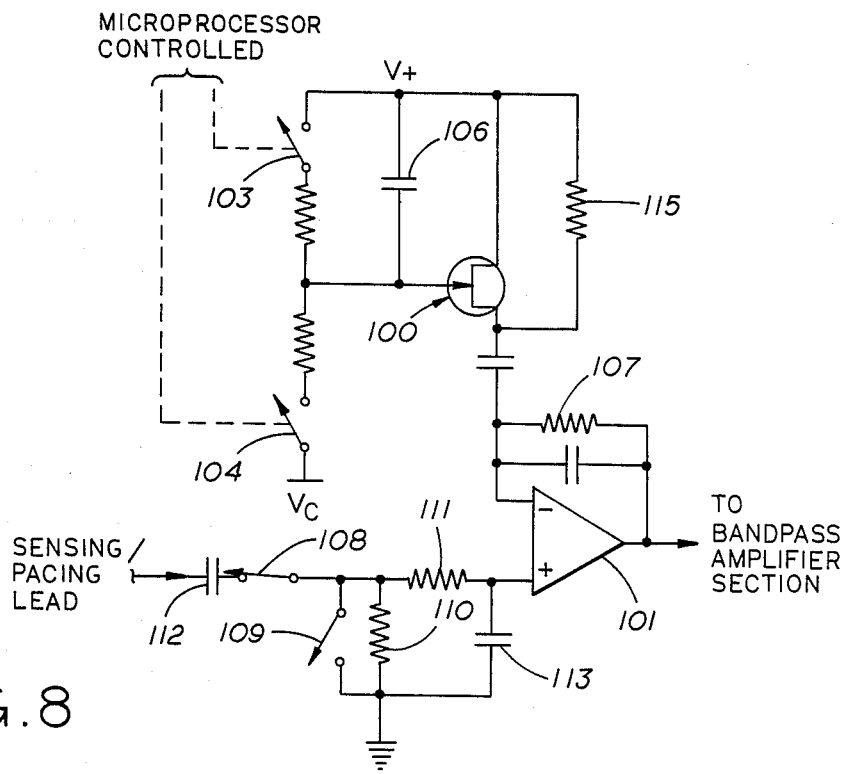
FIGS. 8 through 18, inclusive, are more detailed circuit diagrams of various portions of the preferred embodiment.

Referring to FIG. 8, the AGC amplifier section includes some initial bandpass filtering and a blanking circuit to block the large amplitude pacing and shock signals. This prevents amplifier saturation and thus decreases post-pace amplifier recovery time. The AGC amplifier gain is controlled by varying the gate voltage of an N-channel junction field effect transistor (JFET) 100 which acts as a voltage controlled input resistor to a non-inverting amplifier 101. The microprocessor controls the on/off duty cycle of switches 103 and 104, which set the gate voltage of JFET 100 by charging and discharging capacitor 106 to a voltage between V+ and Vc. This technique is used to obtain a gain range of 60:1 as determined by the resistance of resistor 107 and the on impedance of JFET 100.

Switches 108 and 109 serve to prevent the large amplitude pacing and shock signals from entering the amplifier input. To that end, immediately prior to delivering a pacing or shock output, switch 108 is switched from its normally closed state to an open condition and switch 109 is switched from its normally open state to a closed condition. Consequently, the amplifier 101 input is disconnected from the lead system by switch 108 and grounded by switch 109. The two switches are returned to their normal states a few milliseconds after completion of a pace output and a few hundred milliseconds after completion of a shock output.

The initial bandpass filtering function of the AGC amplifier section is provided by the circuit consisting of resistors 110 and 111 and capacitors 112 and 113. Resistor 115 is used for proper biasing of the JFET circuit.

Although the switches are schematically depicted as mechanical devices in the AGC amplifier circuit of FIG. 8 and in certain of the other circuit diagrams, it will be understood that this is done strictly for the sake of simplifying the drawings, and that in practice electronic switches (such as transistors) typically would be employed.

Referring now to FIG. 9, the bandpass amplifier section of the sense amplifier has a programmable sense margin feature and special bandpass characteristics which aid in tracking the variable amplitude fibrillation signal. The section includes two active bandpass filter amplifiers 130 and 131, a programmable gain DC amplifier 135, and a passive high pass filter comprising capacitor 137 and resistor 138. This bandpass configuration has the advantage of reducing the amplitude of the signal components outside the frequency band of interest, and effectively increasing the sense margin for low frequency fibrillation signals (where higher frequency QRS signals are absent).

In addition, the sense margin (i.e., the ratio between the inner and outer targets to be described below) is also selectable by the microprocessor in that the gain to the inner target comparators can be set separate from that of the outer target comparators, by setting the magnitude of resistance 140 around DC amplifier 135. Alternatively, the effective ratio of the targets may be changed by varying the gain of bandpass filter amplifier 131 (by varying the value of resistor 142 around that amplifier), or by changing the target reference voltages themselves.

Figure 11:
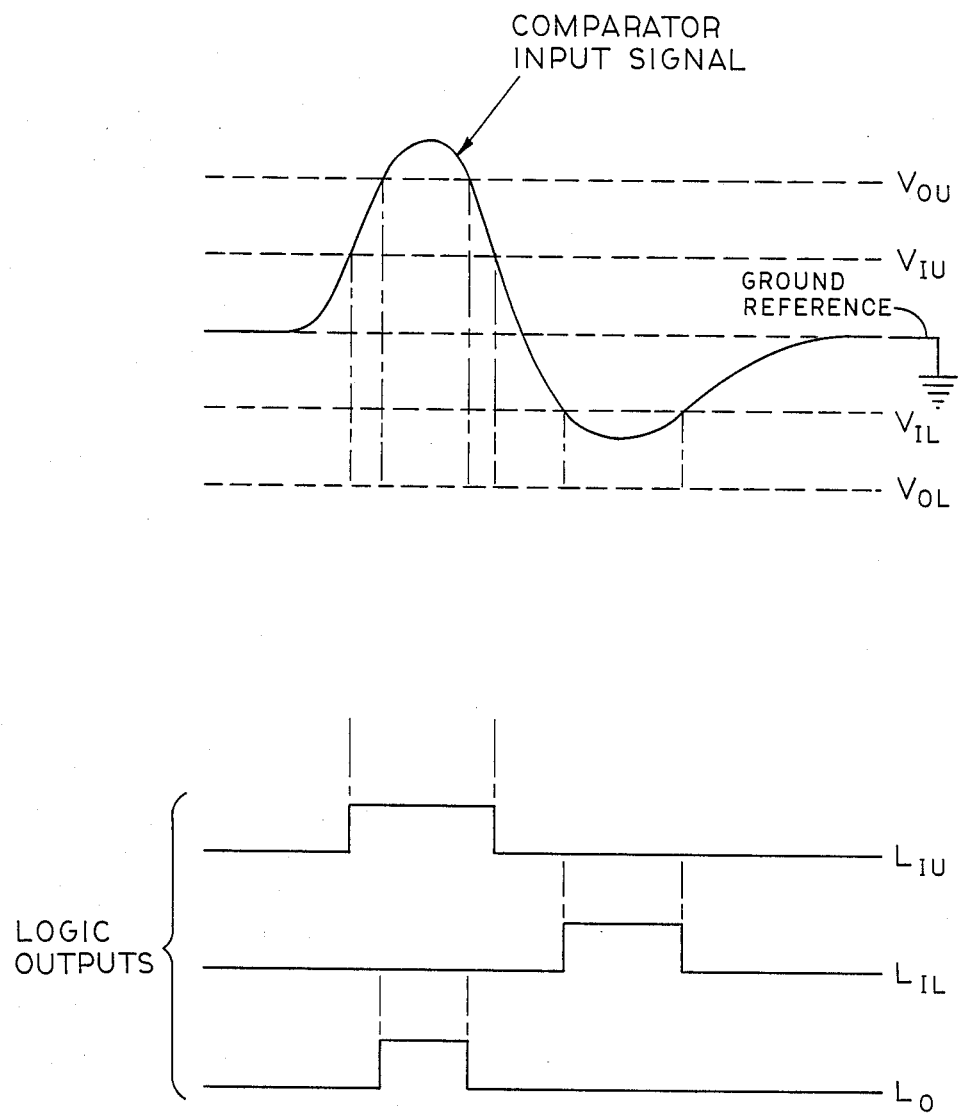

With reference to the circuit diagram of FIG. 10, and the exemplary input signal with logic outputs illustrated in FIG. 11 for the comparator circuit of FIG. 10, the quad comparator section of the sense amplifier consists of two comparator pairs, inner target comparators 150 and outer target comparators 151. The logic outputs $L_{IU}$ and $L_{IL}$ of the inner target comparators are used by the microprocessor as valid sense input signals. The logical "OR" ($L_O$) of the output target comparators is used by the microprocessor to evaluate the need for increasing or decreasing the AGC amplifier gain.

During sinus rhythm, the amplitude of the QRS complex dictates the gain setting of the AGC amplifier because of its relatively large amplitude and its frequency content. The same situation exists during sensing of a tachycardia. However, the presence of the lower frequency fibrillation signal causes an effective doubling of the sense margin (because of the "special bandpass" filters 141 and 142 (FIG. 9)) which permits more reliable tracking of the variable amplitude fibrillation signal.

A problem area that must be considered is the adjustment of gain during bradycardia pacing. In this case, the lack of sensed events could be attributable to slow rate or to an inadequate amplifier gain setting. To determine which of these is responsible, sensing of lower frequency post-pace T-waves is performed. If no T-wave is sensed at the inner target comparators in a preset time window following a pace event, the AGC gain is increased. This is continued until the T-waves are sensed or until the previously undetected rhythm is sensed.

The major difference between AGC gain control using T-waves versus QRS and fibrillation signals is that the T-wave amplitudes are controlled about the inner target comparator instead of the outer target comparator. This insures that the amplifier gain will not be set too high should an intrinsic QRS signal be sensed.

Figure 12:
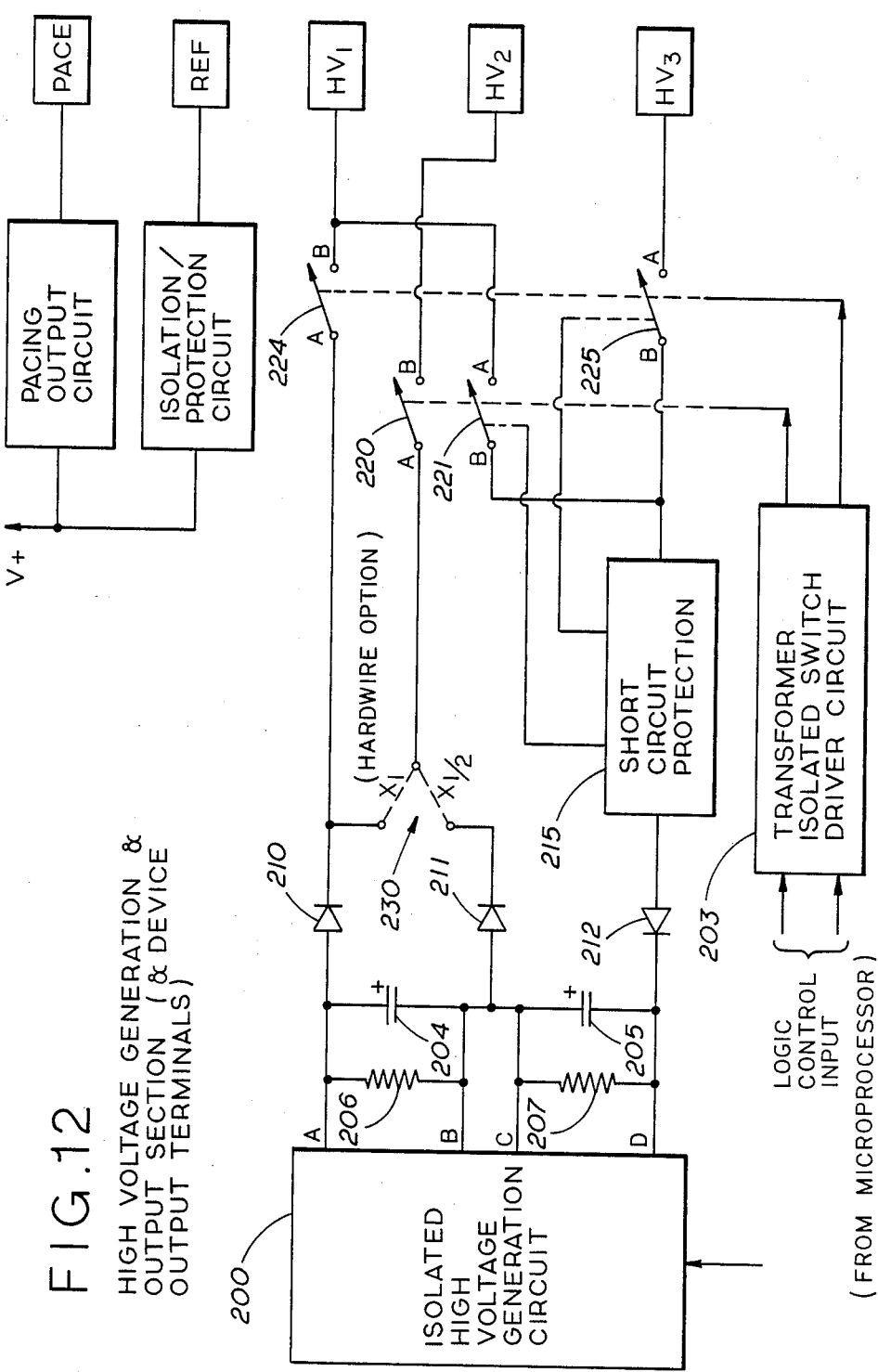

It should be noted that a number of different lead connections are supported by the design of the embodiment described herein. Referring to FIG. 12, the output connections available from the therapy generator are designated "PACE", "REF", "HV1", "HV2" and "HV3". Among the more significant potential lead configurations that may be employed are the following:

(1) One myocardial screw-in or endocardial lead and two titanium (or other conventional material) mesh patches. The myocardial lead is placed on the apex of the left ventricle (LV) or the endocardial lead is placed transvenously at the apex of the right ventricle (RV) (in either instance, connected to "PACE"), one patch on the epicardium of the LV (connected to "REF" and "HV1") and one patch on the epicardium of the RV (connected to "HV2" and "HV3"). Pacing and sensing are from myocardial (anode) to LV patch (cathode). Cardioversion and DF are from LV to RV (right ventricle) patch.

(2) Two myocardial screw-in leads or one bipolar endocardial lead, and two titanium mesh patches. Both myocardial leads are placed in the apex of the ventricles or the bipolar endocardial lead is placed transvenously at the apex of the RV (in either instance, one electrode connected to "PACE" and the other to "REF"), one patch on the epicardium of the left ventricle (connected to "HV1") and one patch on the right ventricle (connected to "HV2" and "HV3"). Pacing and sensing are from myocardial to myocardial lead. Cardioversion and DF are from LV to RV patch.

(3) Same as (1) above, with the patches placed on the pericardium instead of the epicardium.

(4) Same as (2) above, with the patches placed on the pericardium instead of the epicardium.

(5) One two conductor transvenous lead and one titanium mesh patch. The tip electrode of the transvenous lead (connected to "PACE") is placed at the apex of RV, the ring electrode of the transvenous lead (connected to "REF" and "HV1") is placed at the upper part of RV, and the patch (connected to "HV2" and "HV3") is placed epicardially, extra-pericardially or subcutaneously such that shock current will flow through the ventricular septum. Pacing and sensing are between the transvenous tip and ring. Cardioversion and DF are from transvenous ring to patch.

(6) One two conductor transvenous lead and two titanium mesh patches. The tip electrode of the transvenous lead (connected to "PACE") is placed at the apex of the RV, the ring electrode of that lead (connected to "REF" and "HV1") is placed in the upper RV, and the two patches (one connected to "HV2" and the other to "HV3") are placed epicardially, extra-pericardially or subcutaneously on the right and left sides of the ventricles. Pacing and sensing are between the transvenous tip and ring. Cardioversion and DF are from the transvenous ring to each patch (separate waveforms).

(7) One three conductor transvenous lead and one titanium mesh patch. The tip electrode of the transvenous lead (connected to "PACE") is placed at the apex of the RV, distal ring electrode (connected to "HV1" and "REF") is placed in the upper RV, the proximal ring electrode (connected to "HV2") is placed in the superior vena cava, and one patch (connected to "HV3") is placed epicardially, extra-pericardially or subcutaneously such that shock current will flow through the ventricular septum. Pacing and sensing are between the transvenous tip and the distal ring. Cardioversion and DF are from transvenous distal ring to either the proximal ring or the patch (separate output waveforms).

The high voltage generation and output section is illustrated in greater detail in the circuit diagram of FIG. 12. That section comprises an isolated high voltage generation circuit 200, a transformer isolated switch driver circuit 203, two output capacitors 204 and 205 with bleeder resistors 206 and 207, three protection diodes 210, 211 and 212, an output short circuit protection circuit 215, and two pairs of high voltage output switches 220, 221 and 224, 225.

When the need for a shock therapy has been determined, the microprocessor enables the high voltage generation circuit 200 to charge output capacitors 204 and 205 to a preset value. After the charging is completed, the prescribed output shock is delivered by closing the appropriate switch pair. Depending on how HV1, HV2 and HV3 are connected externally, a variety of output combinations can be accomplished. It will be noted that if HV2 and HV3 are connected together, the closing of switch pair 220, 221 produces an output of opposite polarity to that produced by closing switch pair 224, 225. In addition, a hardwire option 230 is included to enable selection of either a full or half amplitude for the output via switch pair 220, 221. This allows the generation of biphasic output waveforms of approximately half the amplitude in one direction compared to the other direction.

Figure 13:
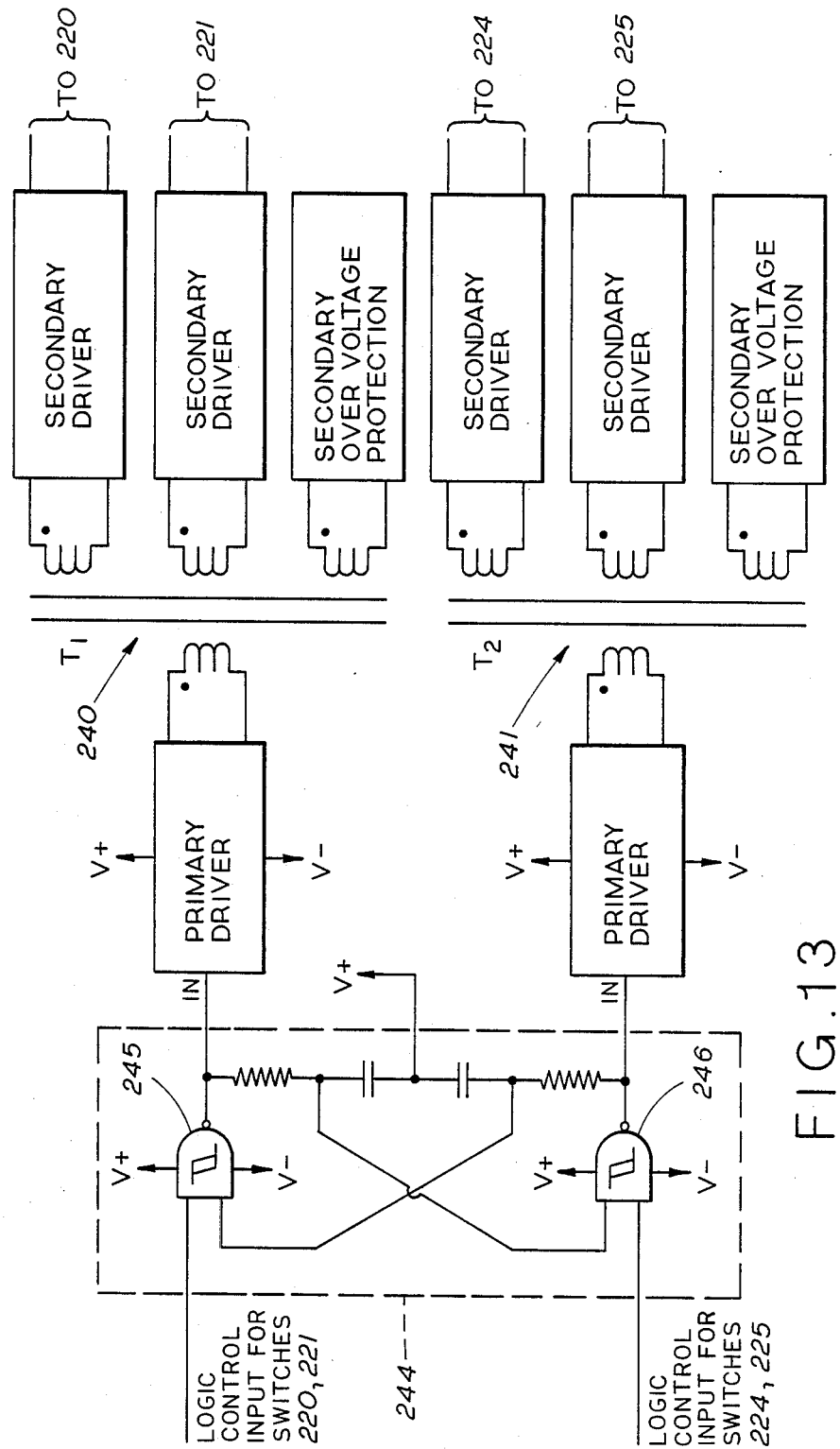

Referring now to FIG. 13, the transformer isolated switch driver circuit 203 comprises two transformers 240 and 241, each having one primary driver circuit, two secondary driver circuits and one secondary overvoltage protection circuit. An input circuit 244 assures non-overlap between the signals controlling the pairs of output switches 220, 221 and 224, 225. Level shifted logic circuits from the microprocessor drive the logic input to the two primary drivers. The transformer isolation provided by 240 and 241 protects the low voltage, low power electronic components from the high voltage outputs.

Figure 14:
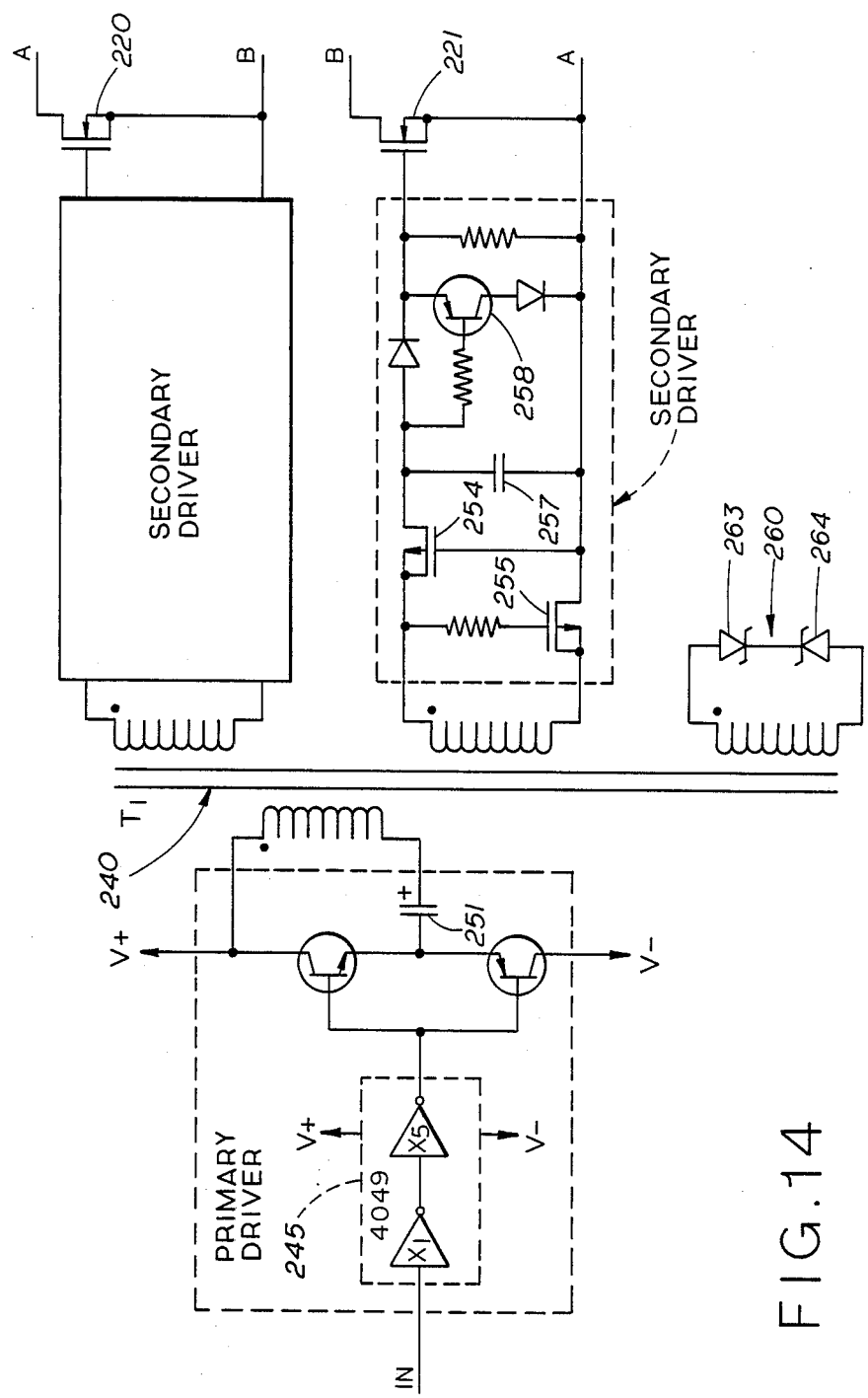

FIG. 14 shows the primary and secondary drivers of each transformer in greater detail, although for the sake of simplicity only the applicable portion of transformer 240 is depicted. The leading edge of a negative logic pulse at the input of the primary driver causes the negative end of capacitor 251 to be pulled from V+ to V−. This transfers energy from the capacitor to the primary coil winding and consequently to the secondary winding (through the ferromagnetic core on which the windings are wound). The result is a positive voltage across the secondary circuit which turns on P-channel transistor 254 and provides forward bias for the parasitic diode across P-channel transistor 255 charging capacitor 257 and the gate capacitance of N-channel transistor (switch) 221 while holding PNP transistor 258 off. The positive voltage at the gate of transistor 221 turns that switch on, allowing current to flow from the output switches to the external load (i.e., the selected lead/electrode configuration and the patient's heart, as described with reference to FIG. 12).

On the trailing edge of the input logic pulse, the negative end of capacitor 251 (which is now fully charged) is pulled to V+, producing a negative voltage across the secondary circuit. This turns on transistor 255 and provides forward bias for the parasitic diode across transistor 254, reverse charging capacitor 257, turning on transistor 258 and dumping the gate capacitance of transistor 221 which turns off that switch. This disconnects the high voltage capacitors 204, 205 (FIG. 12) from the external load, thus ending the shock output pulse. In addition, transistor 258 prevents the gate voltage of transistor 221 from being influenced by capacitively coupled signals impressed on its drain.

The secondary overvoltage protection circuit 260 comprising zener diodes 263 and 264 guarantees that the voltage applied to the secondary driver of the respective transformer (240, in FIG. 14) is not large enough to break down any of the transistors in the switch driver circuit. This permits use of larger transformer winding ratios so that circuit performance is not diminished with partial battery depletion. It should be noted that the 4049 inverters 245, 246 are configured to provide the high current drive requirements of the emitter followers they are driving.

Figure 15:
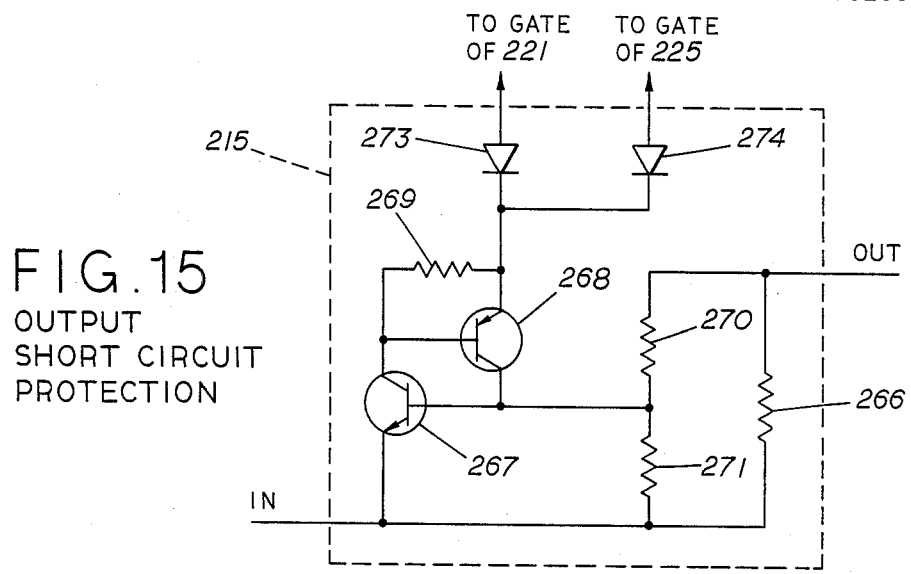

The output short circuit protection circuit 215 of the high voltage generation and output section (FIG. 12) is shown in greater detail in FIG. 15. This protection circuit guards against excessive current flow through (and thus, against damage to) the output switches. Current from the high voltage output capacitors 204, 205 through the output switches to the external load must flow through low impedance resistor 266. Transistors 267 and 268 and resistor 269 form a discrete silicon controlled rectifier (SCR). If the current through resistor 266 increases enough to turn on transistor 267 through the divider consisting of resistors 270, 271, the SCR latches on and pulls down on the gates of output switches 221 and 225 (through diodes 273 and 274), discharging their respective gate capacitances and turning them off. This causes the voltage across resistor 266 to fall because of the reduced current through that resistor, and once the current through the SCR returns to a very low value, the SCR turns off and is ready to be triggered again.

Figure 16:
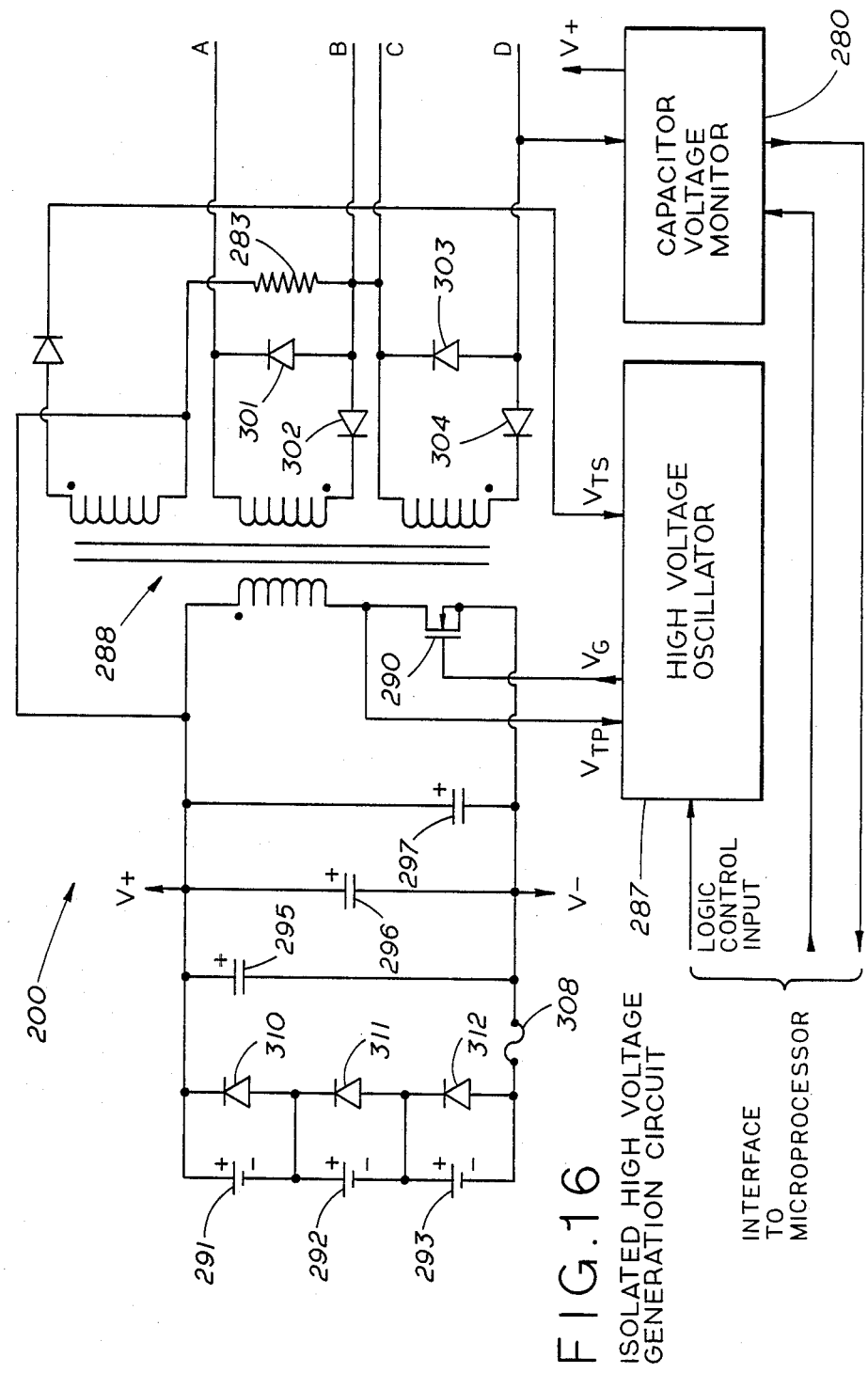

Referring now to FIG. 16, the isolated high voltage generation circuit 200 provides the means to charge the high voltage output capacitors 204, 205 (FIG. 12) to a preset value. The capacitor voltage monitor 280 comprises a digital-to-analog (D/A) converter which is controlled by the microprocessor. The output of the D/A converter goes to one input of a voltage comparator. The other input to the comparator may be connected to a divided down version of the output capacitor voltage for controlling the charge voltage, or to the battery (V−) for battery condition monitoring. A high impedance referencing resistor 283 provides a reference to the V+ voltage.

When configured for capacitor charging, the microprocessor presets the desired voltage value and enables the high voltage oscillator 287 to charge up the capacitors using the flyback circuit comprising transformer 288, N-channel transistor 290, battery cells 291, 292 and 293, filter capacitors 295, 296 and 297, and high voltage oscillator circuit 287. To accomplish this, transistor 290 is turned on and current is allowed to flow through the primary winding of transformer 288. When this current has risen sufficiently, transistor 290 is abruptly turned off and a very large flyback voltage develops across the primary (and consequently across the secondaries) of the transformer. The voltages across the secondaries are half wave rectified by diodes 301, 302, 303, 304, to provide a single direction charge transfer to the capacitors 204 and 205 (FIG. 12), forcing them to charge to a DC voltage.

When the voltage monitor comparator 280 signals the microprocessor that the requested voltage has been reached, the high voltage oscillator 287 is disabled and the output is delivered. It should be noted that the high voltage oscillator is also intermittently disabled by the low voltage regulator circuit to insure priority to the control circuitry power source. Fuse 308 provides protection against overheating of the battery cells 291, 292 and 293 because of excessive current drain caused by some circuit failure. Diodes 310, 311 and 312 provide a low impedance path around a respective battery cell if it becomes depleted. This allows more efficient high voltage charging in the event that one cell has failed. The third secondary of transformer 288 provides a positive voltage source for the high voltage oscillator circuit.

Figure 17:
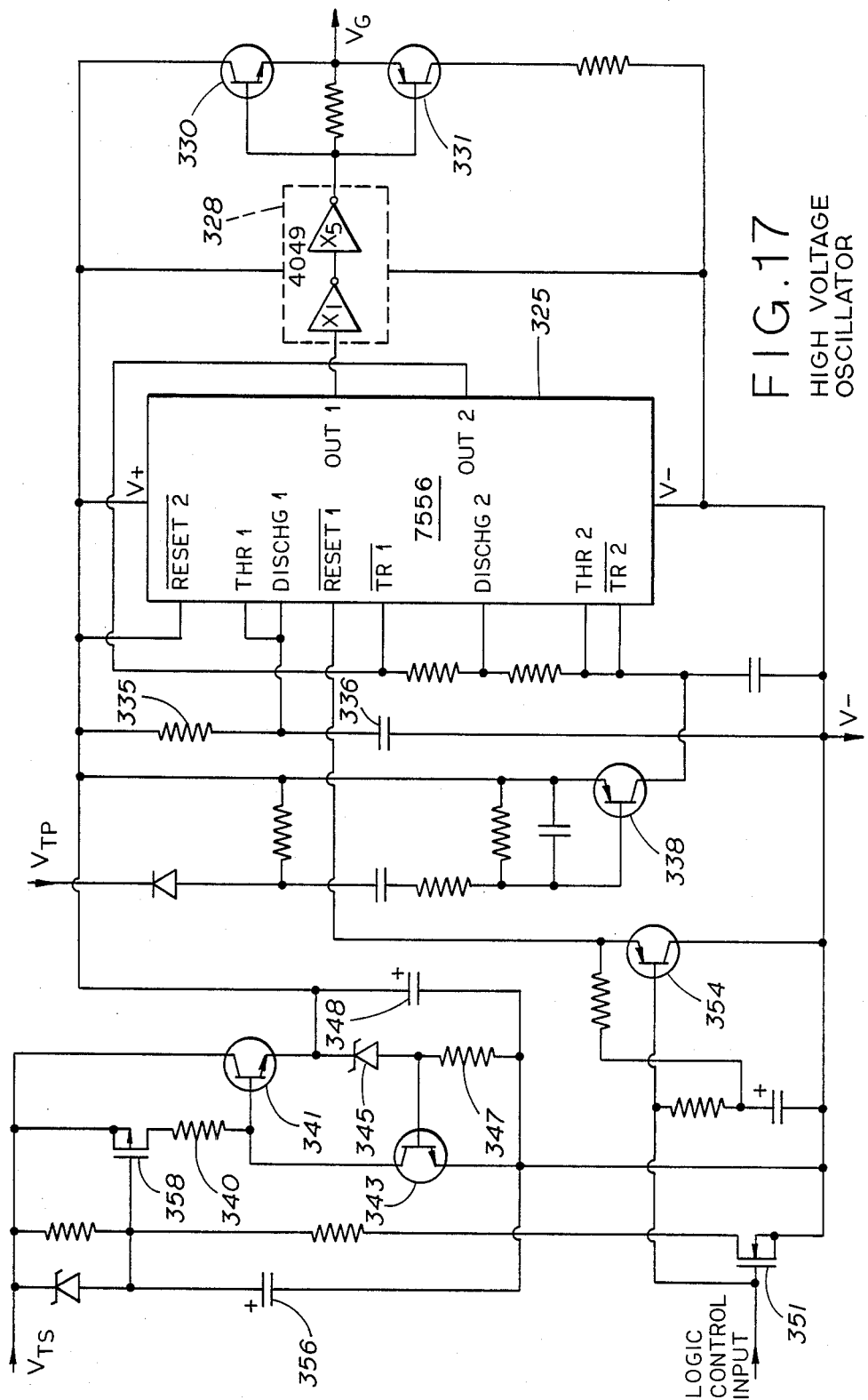

High voltage oscillator circuit 287, illustrated in greater detail in the circuit diagram of FIG. 17, centers around a 7556 timer IC 325 which provides the output pulse train that drives the gate of N-channel transistor 290 (FIG. 16). It will be noted that a high capacitance load driver comprising inverter 328 and transistors 330 and 331, similar to the driver used in the output switch driver circuit (FIG. 14), is used here to drive the gate capacitance of transistor 290 (FIG. 16). This circuit is needed to turn that transistor off fast, which improves the efficiency of the flyback operation. Transistor 290 is also selected to have a very low drain to source "on" impedance since switch drop losses may greatly diminish efficiency.

One-half of timer 325 is configured to run astable at a preset rate determined by associated resistance and capacitance, and to trigger the other half of the timer to produce an output pulse whose duration is determined by resistor 335 and capacitor 336 and which controls the switch driver. As the output capacitors charge up, it becomes easier to transfer energy out of the transformer core. This causes the negative transition of the flyback voltage (occurring at $V_{TP}$) to occur sooner. If this transition occurs before the astable portion of timer 325 times out, transistor 338 is turned on, resetting this timer. In this state, the oscillator continues to speed up as the capacitors complete their charging, producing a more efficient operating condition (since the fixed rate would have resulted in wasted time).

A regulated voltage (generated by resistor 340, transistors 341 and 343, diode 345, resistor 347 and capacitor 348) is provided to the timer IC 325 to make circuit performance independent of battery voltage (over the usable range of the cells). The positive secondary voltage ($V_{TS}$) provides the regulator circuit with ample voltage overhead to make this possible. To enable the high voltage logic circuit, a positive logic signal is applied to the gate of N-channel transistor 351. This turns that transistor on, providing power to the circuit and removing the reset condition (at RESET1 of timer 325). If the low voltage regulator requests that the high voltage oscillator be temporarily disabled, the logic signal at the gate of transistor 351 is brought low which immediately resets the timer 325 (via transistor 354) but does not remove the power to this circuit until capacitor 356 charges up to shut transistor 358 off. This allows short interrupts of the oscillator without disturbing power, which also improves the circuit efficiency.

Figure 18:
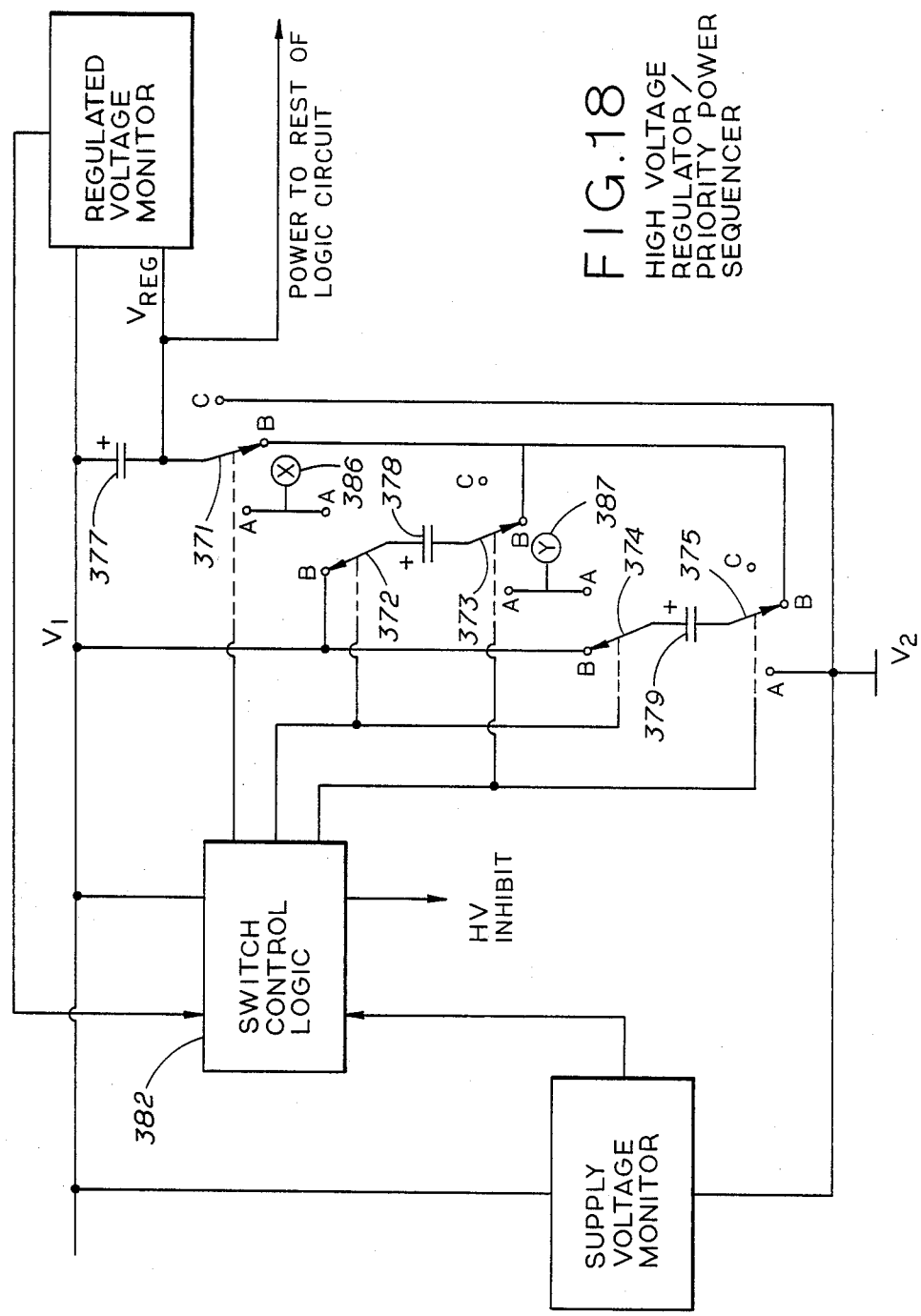

Referring now to FIG. 18, the voltage regulator/power priority sequencer section comprises five switches 371–375 (controlled by low power logic) to charge up a capacitor 377 to a preset value ($V_{reg}$). Capacitors 378 and 379 are much smaller than capacitor 377 and are used in conjunction with capacitor 377 to divide the supply voltage by three, and to transfer charge to the latter capacitor a small amount at a time. When capacitor 377 is being charged, switches 371–375 are switching between their respective A and B states. When the regulated voltage monitor senses that capacitor 377 is at the appropriate voltage level, it signals the switch control logic to go to the standby mode where switches 371, 372 and 374 stay in state B and switches 373 and 375 go to their C state to stop the charging of capacitor 377. The regulated voltage monitor then watches $V_{reg}$ and, via the switch control logic, guarantees that $V_{reg}$ is maintained at this preset value by enabling the charge mode whenever it is needed.

If the supply voltage drops below a level which will support this division by three (i.e., $V_{reg}$ could not be properly regulated), the supply voltage monitor signals the switch control logic section 382 which changes to the direct regulation mode. In this mode, switches 372 and 374 are in state B, switches 373 and 375 are in state C, and switch 371 switches between states B and C, charging capacitor 377 directly from the supply voltage. This mode is much more inefficient but is designed to assure that $V_{reg}$ generation has high priority (even if more power is required).

In addition, if the regulated voltage monitor is requesting that capacitor 377 be charged, switch control logic 382 generates a logic inhibit signal and sends it to the high voltage oscillator circuit (a circuit that causes major drain on the supply when active) and disables its operation until the $V_{reg}$ voltage is back to the desired level. This guarantees that $V_{reg}$ (which provides power to all of the very important control logic for the cardiac stimulator, including the logic that controls the high voltage operation) is given priority to assure safe operation.

If it were desirable to configure the regulator circuit to divide the supply voltage by two instead of three (i.e., use two cells rather than three), capacitor 378 may be left out and a jumper connected between nodes 386 and 387.

The present state of the technology pertaining to high voltage components, such as the battery cells, capacitors, transformers, and so forth, dictates a relatively large package for the therapy generator portion of the cardiac stimulator compared to the smallest present-day pacemaker models. This tends to necessitate implantation of the device in the patient's abdomen, rather than the placement customarily used for a pacemaker, in the pectoral region.

Although a presently preferred embodiment of the invention has been described, it will be apparent from that description to those skilled in the field to which the invention pertains, that variations of the present embodiment may be implemented without departing from the principles of the invention. Further, as technological advances are made, for example, in developing practical small-size, low-cost high voltage components, similar to the advances in the semiconductor field, the principles of the invention may be applied directly to a "universal" implantable device for performing an all-purpose cardiac treatment function.

Accordingly, it is intended that the invention be limited not by the structural or functional elements of the described embodiment, but only as set out in the appended claims.

We claim:

1. An implantable cardiac stimulator, comprising
   means for detecting cardiac arrhythmias in a predetermined heart rate continuum of a patient,
   means responsive to the detection of an arrhythmia for delivering a predetermined therapy regimen from among a multiplicity of available therapy regimens to treat said detected arrhythmia according to the rate thereof, each of said multiplicity of therapy regimens consisting of prescribed electrical stimuli to be delivered to the patient's heart and at least some of said plurality of therapy regimens differing from the others with respect to the aggressiveness of the treatment provided by the respective therapy regimens according to the particular characteristics of the respective stimuli and pattern of delivery thereof, and
   means responsive to a material change of rate of said detected arrhythmia to automatically institute delivery of a different therapy regimen of greater or lesser aggressiveness than that delivered for treatment of the detected arrhythmia prior to said rate change, for treatment of said changed arrhythmia according to whether the rate change is an increase or a decrease from the prior rate, respectively.

2. The cardiac stimulator of claim 1, in which
   said means for detecting arrhythmias includes means for programmably establishing the rate boundaries of the heart rate continuum within which arrhythmias are to be detected.

3. The cardiac stimulator of claim 2, in which
   said means for programmably establishing further permits programmably establishing the rate boundaries of a plurality of classes of tachyarrhythmias of contiguous, progressively higher rate ranges within said heart rate continuum.

4. The cardiac stimulator of claim 3, in which
   said delivering means includes means for controllably modifying the aggressiveness of the selected therapy regimen during treatment of a detected tachyarrhythmia.

5. The cardiac stimulator of claim 4, in which
   said means for controllably modifying prevents the return to a therapy less aggressive than that last delivered, upon acceleration of the tachyarrhythmia to a higher class.

6. The cardiac stimulator of claim 4, in which
   said means for controllably modifying produces a repetition of the least aggressive therapies within the previously delivered therapy regimen before proceeding to a redelivery of the entire therapy regimen.

7. The cardiac stimulator of claim 2, in which
   said means for detecting further includes means for selectively establishing criteria for detecting each of the potential episodes of bradycardia, tachycardia, fibrillation, and reversion to sinus rate.

8. The cardiac stimulator of claim 7, in which
   said means for establishing criteria for detecting tachycardias utilizes the basic criteria of high heart rate, sudden onset of the high rate, stability of the high rate, and sustained high rate.

9. The cardiac stimulator of claim 7, in which
   said means for establishing criteria for detecting fibrillation utilizes the basic criteria of high heart rate exceeding the highest rate for detecting tachycardias, and the occurrence of at least x fibrillation intervals out of y consecutive intervals, where x and y are selectible.

10. The cardiac stimulator of claim 3, in which
    further including means for redetecting the presence or absence of the earlier detected arrhythmia following delivery of a therapy regimen, said redetecting means being responsive to a change of class of said earlier detected arrhythmia as indicative of said material change of rate.

11. The cardiac stimulator of claim 10, in which
    said redetecting means distinguishes an actual acceleration of the redetected arrhythmia to the next higher class from a false indication of such acceleration.

12. The cardiac stimulator of claim 1, in which
    said means for delivering includes means for controllably modifying the aggressiveness of the selected therapy regimen during treatment of the detected arrhythmia.

13. The cardiac stimulator of claim 1, in which
    said means for delivering includes means for controllably reapplying a therapy identical to that previously applied in response to detection of an arrhythmia, upon the very next incidence of an arrhythmia.

14. The cardiac stimulator of claim 13, in which said reapplied therapy is identical to the entire last therapy regimen successful in terminating a tachycardia.

15. The cardiac stimulator of claim 13, in which
said reapplied therapy is identical to the last therapy of the overall therapy regimen last successful in terminating a tachycardia.

16. An implantable medical device for treating cardiac arrhythmias, comprising
means for dividing the heart rate spectrum into at least three contiguous, successive regions of progressively higher rate ranges, each of said regions representative of a respective class of arrhythmia,
means for detecting anywhere within said spectrum an arrhythmia of a patient's heart,
means for programmably assigning therapies in a regimen for each class according to the rate range thereof, different from the therapy regimens for the other classes, to treat the detected arrhythmia according to the class thereof, and.
means responsive to said detected arrhythmia for automatically delivering at least one of the therapies assigned to the respective class of that arrhythmia for application to the patient's heart.

17. The device according to claim 16, further including
means responsive to detection of an arrhythmia outside either of the upper and lower boundaries of the continuum of said regions, for automatically delivering first or second preselected therapies according to whether said activity is outside said upper boundary or said lower boundary, respectively,
said first and second therapies being different in kind from each other and different in degree from the preselected therapy regimens assigned to said regions.

18. The device according to claim 16, further including
means for automatically modifying the preselected therapy regimen to be delivered for any particular class of arrhythmia according to a predetermined therapy control function, in response to the effect of the immediately preceding regimen on the arrhythmia under treatment, during the period said arrhythmia is in progress.

19. The device according to claim 18, in which said arrhyhmias to be treated are tachyarrhythmias,
said means for automatically modifying delivering progressively more aggressive regimens until the tachyarrhythmia under treatment is terminated.

20. The device according to claim 18, in which said arrhythmias to be treated are tachyarrhythmias,
said means for automatically modifying being responsive to the detection of the tachyarrhythmia under treatment as of a rate appearing to be hemodynamically tolerated, to apply a preselected number of repetitions of the less aggressive therapies within the applicable preselected regimen before proceeding to apply the more aggressive therapies within said regimen.

21. A cardiac stimulator for detecting and treating tachyarrhythmias, comprising
means for selectively dividing the heart rate continuum into at least two classes of tachycardia, contiguous to each other and of progressively higher heart rate ranges, the lowest and highest of said classes being bounded respectively by a sinus rate region and a fibrillation region of the continuum,
means for selectively adjusting the boundaries between said classes and between the lowest and highest of said classes and the respective sinus rate and fibrillation regions, to correspondingly vary the rate ranges of said classes in a desired manner,
means for selectively detecting cardiac episodes within any of said classes and for distinguishing between normal and abnormal tachycardias among such episodes, and
means responsive to detection of an abnormal tachycardia for selectively treating same with any of a multiplicity of therapy regimens of selectively varying aggressiveness toward terminating said detected tachycardia.

22. The cardiac stimulator of claim 21, in which
said treating means includes means responsive to acceleration of a detected tachycardia into said fibrillation region for automatically applying defibrillation therapy to the patient's heart.

23. The cardiac stimulator of claim 21 or claim 22, in which
said detecting means includes means for sensing a loss of electrical activity of the patient's heart, and
said treating means includes means responsive to the sensed loss of electrical activity for automatically applying electrical stimulating pulses to the heart for pacing the heart until resumption of the heart's normal electrical activity.

24. The cardiac stimulator of claim 21, further including
means for programmably controlling the sequence in which therapies in said regimens are applied by said treating means in response to detection of an abnormal tachycardia within any of said classes.

25. The cardiac stimulator of claim 21, in which
said detecting means includes means for selectively redetecting the presence or absence of an abnormal tachycardia in any of said classes after each application of a therapy regimen by said treating means, said redetecting means applying only some of the criteria applied by said detecting means for the initial detection of the tachycardia.

26. The cardiac stimulator of claim 21, in which
said detecting means includes means for sensing acceleration of the rate of a detected tachycardia to a higher one of said classes, and
said treating means is responsive to the sensed acceleration to thereupon deliver a therapy regimen preselected for a tachycardia of said higher class.

27. The cardiac stimulator of claim 21, in which
said therapy regimens include both pacing therapy and shock therapy, the two types of therapy differing in at least the level of electrical energy applied to the heart.

28. The cardiac stimulator of claim 27, in which
each of said pacing and shock therapies is selectively variable in at least one characteristic of the electrical waveform constituting a portion of the respective therapy.

29. The cardiac stimulator of claim 21, in which
said detecting means includes means for sensing reversion of the patient's heart rate to sinus rhythm.

30. An implantable medical device for treating cardiac arrhythmias, comprising
means for dividing the heart rate continuum into a plurality of contiguous, progressively higher rate ranges bounded by rates indicative of normal sinus rhythm and fibrillation, respectively, by which to classify an arrhythmia according to rate range within which it arises, means for detecting anywhere within said rate continuum an arrhythmia, said detecting means including means for applying different detection criteria to the different rate ranges, said different detecting criteria being progressively less stringent as said rate ranges become progressively higher, to reflect the increasing hemodynamic intolerance with increasing rate of the arrhythmia and means for stimulating the heart responsive to the detection of an arrhythmia.

31. The medical device of claim 30, in which said detecting means further includes means for eliminating at least some of said detecting criteria for redetecting the presence or absence of the previously detected arrhythmia upon treatment thereof, to expedite the redetection.

32. The medical device of claim 30, in which said detecting means includes means for distinguishing said arrhythmia from a normal cardiac episode within at least some of said rate ranges.

33. The medical device of claim 32, in which said detecting means further includes means for detecting a change in rate of said arrhythmia from one of said rate ranges to another.

34. The medical device of claim 33, in which said rate change detecting means includes means for detecting a change in rate of said arrhythmia to an arrhythmia outside said rate ranges.

35. The medical device of claim 32, in which said rate change detecting means further includes means for distinguishing an actual acceleration of the detected arrhythmia to a higher rate range from a false indication of such acceleration.

36. An implantable therapy generator for treating ventricular arrhythmias, comprising means for programmably dividing the heart rate continuum into a plurality of contiguous rate ranges each representing a different tachycardia class by selectively assigning a rate to the boundary between adjacent pairs of the rate ranges, said plurality of rate ranges being bounded at the lower end by a sinus rate region and at the upper end by a fibrillation rate region, means for detecting a tachycardia within any of the tachycardia classes and for distinguishing whether said tachycardia is a normal or abnormal cardiac episode, and means responsive to detection of said tachycardia as an abnormal cardiac episode for delivering to the heart a therapy regimen selected according to the class in which said tachycardia is detected, said regimen differing from at least one of the regimens available to be delivered in response to detection of an abnormal cardiac episode in another of the tachycardia classes.

37. The implantable therapy generator of claim 36, further including means for detecting an acceleration of an abnormal cardiac episode into said fibrillation region, and means responsive to detection of said acceleration for delivering a defibrillating therapy.

38. The implantable therapy generator of claim 37, further including means for detecting an absence of cardiac activity following delivery of said defibrillating therapy, and means responsive to said detection of an absence of cardiac activity for delivering stimulating pulses to reestablish normal cardiac activity.

39. The implantable therapy generator of claim 36, in which said detecting means includes means for redetecting the abnormal cardiac episode following delivery of said therapy regimen, and said therapy regimen delivering means includes means for redelivering a therapy regimen upon redetection of the abnormal cardiac episode, consistent with the class in which said episode is redetected.

40. The implantable therapy generator of claim 36, further including means for modifying the criterion for detecting a tachycardia within a class after delivery of said therapy regimen.

41. The implantable therapy generator of claim 36, in which said detecting means includes means for establishing detection criteria for each of said tachycardia classes, ranging from the most stringent of said criteria for the class having the lowest rate range to the most relaxed of said criteria for the class having the highest rate range.

42. The implantable therapy generator of claim 39, further including means for detecting a return of cardiac activity to said sinus rate region after each delivery of a therapy regimen.

43. The implantable therapy generator of claim 36, in which said means for delivering a therapy regimen includes means for repetitively delivering the same therapy regimen in response to repeated redetection of said abnormal cardiac episode within the same tachycardia class, and for delivering a different therapy regimen in response to redetection of said abnormal cardiac episode as having undergone a change of rate to a different class.

44. The implantable therapy generator of claim 43, further including means for selectively establishing the aggressiveness of the therapy regimens with which detected abnormal cardiac episodes are treated.

45. The implantable therapy generator of claim 44, further including means for modifying the previously established aggressiveness of a therapy regimen while a detected abnormal cardiac episode is in progress.

46. The implantable therapy generator of claim 36, in which said detecting means further includes means for detecting a bradycardia, and said therapy regimen delivering means further includes means responsive to detection of a bradycardia for delivering pacing therapy.

47. The implantable therapy generator of claim 36, in which said detecting means further includes means for detecting an arrhythmia within said fibrillation region, and means responsive to detection of an arrhythmia within said fibrillation region for delivering defibrillation therapy.

48. The implantable therapy generator of claim 36, in which said therapy regimen delivering means is selectively adjustable to deliver pacing therapy, shock therapy or a combination of pacing therapy and shock therapy as the therapy regimen to be delivered in response to detection of an abnormal cardiac episode in each of the tachycardia classes.

49. An implantable medical device for treating ventricular cardiac arrhythmias, comprising
means for programmably dividing a predetermined portion of the heart rate spectrum into a plurality of contiguous, successive regions of progressively higher rate ranges, each region representing a respective class of ventricular tachyarrhythmia,
means for detecting anywhere within the predetermined portion of the heart rate spectrum a tachyarrhythmia of a patient's heart,
means responsive to the detected tachyarrhythmia for automatically delivering a preselected therapy regimen comprising electrical stimuli, adapted to be applied to the ventricles of the patient's heart, according to the respective class of the detected tachyarrhythmia, the delivered regimen differing from at least some of a plurality of available preselected therapy regimens respectively assigned to others of said regions for application to the patient's heart in response to tachyarrhythmias detected in said other regions.

50. The device according to claim 49, wherein said dividing means includes means for selectively partitioning said heart rate spectrum into at least two contiguous regions with rate ranges representing ventricular tachycardias and with variable rate boundaries therebetween, in which the progressively higher rate ranges thereof are indicative of the degree of hemodynamic tolerance of the patient to heart rates within those regions, ranging from well tolerated in the lowest to poorly tolerated in the highest of said at least two regions.

51. The device according to claim 49, wherein said detecting means includes
means representing a plurality of algorithms for detecting tacharrhythmias in said regions, and
means for selecting from among said represented algorithms the algorithms which are to be used for detecting tachyarrhythmias in respective ones of said regions.

52. The device according to claim 49, wherein said therapy regimen delivering means includes
means for selecting one or more individual therapies in any of a multiplicity of different sequences for said delivery, each sequence defining a therapy regimen differing from the therapy regimens defined by others of said different sequences, and
means for selectively altering the characteristics of each therapy according to the particular treatment to be applied thereby within the delivered therapy regimen toward arresting the tachyarrhythmia and returning the heart rate to that within the rate range considered normal for the particular patient.

53. The device according to claim 52, wherein said selectively altering means includes
means for altering any therapy consisting of either cardioverting shocks or defibrillating shocks by any of the features in the group consisting of (i) the number of shocks to be delivered, (ii) the delay time interval between detection of the cardiac event and delivery of the shock, (iii) the amplitude of the shocks on the first attempt and each succeeding attempt to arrest the tachyarrhythmia, and (iv) the phasic structure of the shock waveform including pulse width, polarity, presence and absence of each phase.

54. The device according to claim 52, wherein the selectively altering means includes
means for altering any pacing therapy by any of the features in the group consisting of (i) the number of attempts to arrest the detected tachyarrhythmia, (ii) the number of pulses in the burst of pacing stimuli, (iii) the delay time interval between detection and the initial pulse in the burst of pacing stimuli, (iv) the interval between pulses in a burst of pacing stimuli, (v) the automatic decrementing or alternate incrementing and decrementing of either of said delay time interval or said interval between pulses, (vi) the variation of each of said intervals as a percentage of the tachyarrhythmia rate, (vii) the amount by which each of said intervals is increased or decreased for each successive burst, and the number of such increases and decreases, and (viii) the number of times any of the sequences defined by (v), (vi) and (vii) are to be repeated.

55. The device according to claim 49, wherein said therapy regimen delivering means includes
means for selectively assembling any of a multiplicity of different therapy regimens each including one or more therapies in the form of electrical stimuli from the group consisting of (i) bursts of electrical pacing stimuli of varying degrees of aggressiveness based on the vigorousness of the stimulation applied to the heart, (ii) electrical cardioverting shocks of greater intensity than electrical pacing stimuli but less than or equal energy content relative to electrical defibrillating shocks, and (iii) electrical defibrillating shocks; wherein the progression of therapies from the least aggressive pacing burst, to the more aggressive and the most aggressive pacing bursts, to cardioverting shocks, to defibrillating shocks, defines the progression of therapies from the least to the most aggressive.

56. The device according to claim 55, further including
means for applying electrical pacing stimuli to the patient's heart in response to either bradycardia or absence of a heart beat following delivery of a defibrillating shock to the heart.

57. The device according to claim 55, wherein said therapy regimen delivering means further includes
means responsive to continuing detection of the tachyarrhythmia beyond a predetermined number of cardiac cycles for automatically delivering a therapy regimen more aggressive than that delivered prior to the commencement of said predetermined number of cardiac cycles, but within the plurality of therapy regimens assigned to the region within which the rate of the detected tachyarrhythmia lies.

58. The device according to claim 55, wherein said therapy regimen delivering means further includes
means for preselecting the response of the therapy regimen delivering means to a transition of the detected tachyarrhythmia to a new region, comprising promptly halting the therapy regimen under delivery at or prior to the transition and commencing delivery of the least aggressive therapy regimen assigned to the new region.

59. The device according to claim 58, wherein said therapy regimen delivering means further includes means responsive to rate acceleration of the tachyarrhythmia for automatically delivering a therapy regimen at least as aggressive as that delivered prior to the latest rate acceleration, but within the plurality of therapy regimens assigned to the region whose rate range encompasses the then-current rate of the tachyarrhythmia.

60. The device according to claim 59, wherein the preselected response of said preselecting means further includes, if the tachyarrhythmia thereafter continues at a rate in the new region, following with delivery of the next more aggressive therapy regimen assigned to the new region.

61. The device according to claim 49, further including
    means for programming said device to permit patient activated capture test, and interrogation of elective replacement status and end of service status.

62. The device according to claim 49, wherein said therapy regimen delivering means includes
    means for generating high voltage levels suitable for delivery of cardioverting shocks and defibrillating shocks to the patient's heart.

63. The device according to claim 62, wherein said high voltage generating means includes
    high voltage capacitors,
    a high voltage oscillator, and
    isolation means coupling said oscillator to said capacitors for charging thereof to respective ones of said high voltage levels of cardioverting shocks and defibrillating shocks.

64. The device according to claim 63, wherein said high voltage generating means further includes
    output circuit means for delivering said high voltage shocks to the patient's heart, and
    switch means operable to apply the high voltages on said capacitors as pulses of desired amplitude and polarity to said output circuit means;
    and wherein said device further includes
    control means for selectively operating said switch means.

65. The device according to claim 64, wherein said high voltage generating means further includes
    short circuit protection means for opening said output circuit means in response to current flow exceeding a predetermined level in said output circuit means.

* * * * *

REEXAMINATION CERTIFICATE (3361st)

United States Patent [19]

Haluska et al.

[11] B1 4,830,006

[45] Certificate Issued  Oct. 28, 1997

[54] IMPLANTABLE CARDIAC STIMULATOR FOR DETECTION AND TREATMENT OF VENTRICULAR ARRHYTHMIAS

[75] Inventors: Edward A. Haluska, Angleton; Stephen J. Whistler, Lake Jackson; Ross G. Baker, Jr.; Richard V. Calfee, both of Houston, all of Tex.

[73] Assignee: Intermedics, Inc., Angleton, Tex.

Reexamination Requests:
No. 90/004,261, Jun. 10, 1996
No. 90/004,356, Sep. 5, 1996

Reexamination Certificate for:
Patent No.: 4,830,006
Issued: May 16, 1989
Appl. No.: 875,218
Filed: Jun. 17, 1986

[51] Int. Cl.$^6$ .................................... A61N 1/39
[52] U.S. Cl. ......................................... 607/4
[58] Field of Search ..................... 607/4, 5, 12, 14, 607/15, 17, 25, 28

[56] References Cited

U.S. PATENT DOCUMENTS

| | | |
|---|---|---|
| Re. 30,750 | 9/1981 | Diack et al. . |
| 3,144,019 | 8/1964 | Haber . |
| 3,703,900 | 11/1972 | Holznagel . |
| 3,717,140 | 2/1973 | Greenwood . |
| 3,724,455 | 4/1973 | Unger . |
| 3,857,398 | 12/1974 | Rubin . |
| 3,881,467 | 5/1975 | Stanely et al. . |
| 4,030,509 | 6/1977 | Heilman . |
| 4,088,138 | 5/1978 | Diack et al. . |
| 4,184,493 | 1/1980 | Langer et al. . |
| 4,202,340 | 5/1980 | Langer et al. . |
| 4,223,678 | 9/1980 | Langer et al. . |
| 4,316,472 | 2/1982 | Mirowski et al. . |
| 4,384,585 | 5/1983 | Zipes . |

(List continued on next page.)

FOREIGN PATENT DOCUMENTS

| | | |
|---|---|---|
| 1160296 | 1/1984 | Canada . |
| 0023134 | 1/1981 | European Pat. Off. . |
| 1144706 | 3/1985 | U.S.S.R. . |
| 1149979 | 4/1985 | U.S.S.R. . |
| 1178456 | 9/1985 | U.S.S.R. . |
| 1263260 | 10/1986 | U.S.S.R. . |

OTHER PUBLICATIONS

*Physician's Manual*, Intermedics' Intertach Model 262–12 Bipolar, Multi–programmable, Antitachycardia Cardiac Pulse Generator (1984).

Pless and Sweeney, PACE, "Discrimination of Supraventricular Tachycardia from Sinus Tachycardia of Overlapping Cycle Length" (Nov.–Dec. 1984), pp. 1318–1324.

Abstracts 189–192, *PACE*, vol. 8, p. A–48 (May–Jun. 1985).

Abstracts 109–116, *PACE*, vol. 9, pp. 302–303, (Mar.–Apr. 1986).

Arzbaecher, R. et al., *PACE*, vol. 7, pp. 541–547 (May–Jun. 1984).

(List continued on next page.)

*Primary Examiner*—George Manuel

[57] ABSTRACT

An implantable cardiac stimulator integrates the functions of bradycardia and anti-tachycardia pacing-type therapies, and cardioversion and defibrillation shock-type therapies. The stimulator is programmable to provide a multiplicity of hierarchical detection algorithms and therapeutic modalities to detect and treat classes of ventricular tachycardia according to position within rate range classes into which the heart rate continuum is partitioned, and thus according to hemodynamic tolerance, with backup capabilities of defibrillation and bradycardia pacing at the higher and lower regions of the rate continuum outside the range of the ventricular tachycardia classes. Aggressiveness of the therapy is increased with elapsed time and increasing heart rate, and detection criteria are relaxed with increasing heart rate and thus with increasing hemodynamic intolerance of the tachycardia.

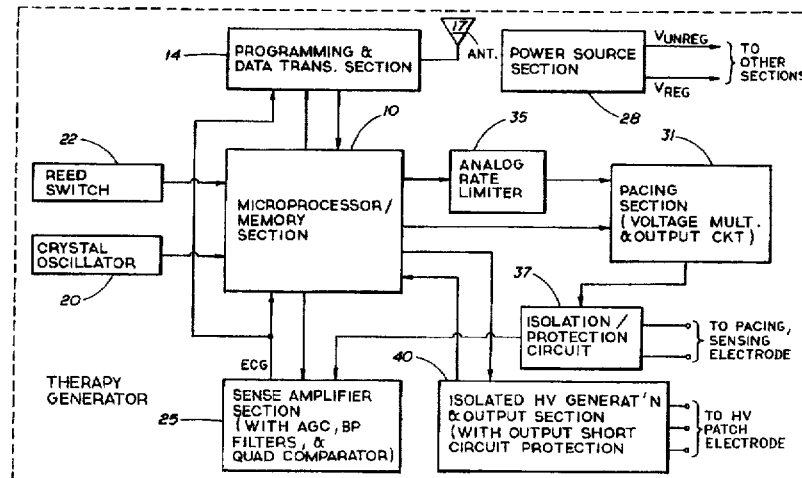

U.S. PATENT DOCUMENTS

| | | |
|---|---|---|
| 4,403,614 | 9/1983 | Engle et al. |
| 4,407,288 | 10/1983 | Langer et al. |
| 4,456,959 | 6/1984 | Hirano et al. |
| 4,466,440 | 8/1984 | Money et al. |
| 4,475,551 | 10/1984 | Langer et al. |
| 4,503,857 | 3/1985 | Boute et al. |
| 4,559,946 | 12/1985 | Mower. |
| 4,567,900 | 2/1986 | Moore. |
| 4,647,217 | 3/1987 | Havel. |
| 4,667,682 | 5/1987 | Ihlenfeld. |
| 4,686,989 | 8/1987 | Smyth et al. |
| 4,688,573 | 8/1987 | Alt. |
| 4,693,253 | 9/1987 | Adams. |
| 4,705,043 | 11/1987 | Imran. |
| 4,708,144 | 11/1987 | Hamilton et al. |
| 4,726,380 | 2/1988 | Vollmann et al. |
| 4,741,342 | 5/1988 | Stotts. |
| 4,754,753 | 7/1988 | King. |
| 4,779,617 | 10/1988 | Whigham. |
| 4,781,194 | 11/1988 | Elmqvist. |
| 4,819,643 | 4/1989 | Menken. |
| 4,827,936 | 5/1989 | Pless et al. |
| 4,850,357 | 7/1989 | Bach, Jr. |
| 4,860,751 | 8/1989 | Callaghan. |
| 4,880,005 | 11/1989 | Pless et al. |
| 4,913,146 | 4/1990 | DeCote, Jr. |
| 4,919,137 | 4/1990 | Schaldach. |
| 4,936,304 | 6/1990 | Kresh et al. |
| 4,994,300 | 2/1991 | Saksena. |

OTHER PUBLICATIONS

Camm, A.J. et al., Pacing for Tachycardia Control, Ch. 9, pp. 135–144, *Telectronics* (1983).

Check, W.A., *Medical World News*, pp. 88–111 (Jun. 10, 1985).

Ellenbogen, K.A. et al. *Am. J. Cardiology*, 65: 1105–11 (May 1, 1990).

Epstein, S.E. et al., *Circulation*, vol. XLVII, pp.446–454 (Mar. 1973).

Epstein et al., J. Am. Coll. Cardiol., 13:121–31 (1989).

Fisher, J.D. et al., *Proc. of the 5th Int'l Symposium*, Tokyo, Mar. 14–18 (1976).

Fisher, J.D. et al., *Am. Heart J.*, 93(5):658–68 (May 1977).

Fisher, J.D. et al., *PACE*, vol. 7, pp. 1278–1290 (Nov.–Dec. 1984).

Hauser, R.G., et al., *PACE*, vol. 7, pp. 611–616 (May–Jun. 1984).

Intermedics Annual Report 1986.

Intermedics Intertach Physician's Manual.

Jenkins, J. et al., *Proc. Computers in Cariology, IEEE*, pp. 305–309 (1977).

Jenkins, J.M. et al., *Circulation*, 60(5):977–87 (1979).

Manz, M. et al., PACE, 9:676–84 (Sep./Oct. 1986).

Mehra, R., IEEE Engineering in Medicine & Biology Magazine, pp. 29–34 (Jun. 1984).

Mirowski, M., M. Am. Coll. Cardiol., 6:461–66 (Aug. 1985).

Naccarelli, M.D. et al., *Am. Heart J.*, 105(1):1–5 (Jan. 1983).

Nathan, A.W., et al., *Clin. Cardiol.*, 5:22–26 (1982).

Nathan, A.W., et al., *Eur. Heart J.*, 5:993–1003 (1984).

Pekarsty et al., PACE, 9:1349–55 (Nov./Dec. 1986).

Perelman, M.S. et al., Br. Heart J., 52:385–91 (1984).

Pless, B.D. et al., PACE, 7:1318–24 (Nov./Dec. 1984).

Reddy, C.P. et al., *JACC*, 3(1):225–30 (Jan. 1984).

Reid, P.R. et al., *Am. J. Cardiology*, 51:1608–13 (Jun. 1983).

Rubin, L. et al., *Suppl. II to Circulation*, vol. XLV and XLVI, pp. II–107, (Oct. 1972).

Saksena, S. et al., *PACE*, vol. 8, pp. 715–731 (Sep.–Oct. 1985).

Spurrell, R.A.J. et al., *PACE*, vol. 7, pp. 1296–1300 (Nov.–Dec. 1984).

Stavish, S., CARDIO, pp. 44–46 (Apr. 1985).

Ward, D.E. et al., PACE, 3:178–91 (Mar./Apr. 1980).

Waspe, L.E. et al., Am. J. Cardiol., 52:477–84 (1983).

Weiss, J.N., et al., *Western J. Med.*, vol. 141, No. 5, pp. 649–665 (Nov. 1984).

Wenger, N.K., *PACE*, vol. 7, pp. 569–571 (May–Jun. 1984).

Winkle, R.A., PACE, vol. 7, pp. 1375–1379 (Nov.–Dec. 1984).

Wood, M.A. et al., *Am. J. Cardiology*, 66:575–82 (Sep. 1, 1990).

Zipes, D.P. et al., *PACE*, vol. 7, pp. 522–533 (May–Jun. 1984).

Zipes, D.P. et al., *PACE*, vol. 7, pp. 606–610 (May–Jun. 1984).

Zipes, D.P. et al. *N. Engl. J. Med.*, 311(8):485–490 (Aug. 23, 1984).

Zipes, D.P. et al., *PACE*, 7:1325–30 (Nov.–Dec. 1984).

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–65 is confirmed.

* * * * *